United States Patent
Sheldon et al.

(10) Patent No.: US 7,894,898 B2
(45) Date of Patent: *Feb. 22, 2011

(54) SYSTEM AND METHOD FOR VENTRICULAR INTERVAL SMOOTHING FOLLOWING A PREMATURE VENTRICULAR CONTRACTION

(75) Inventors: Todd J. Sheldon, North Oaks, MN (US); Paul A. Belk, Maple Grove, MN (US); Michael O. Sweeney, Brookline, MA (US)

(73) Assignee: Medtronic, Inc., Minneapolis, MN (US)

( * ) Notice: Subject to any disclaimer, the term of this patent is extended or adjusted under 35 U.S.C. 154(b) by 1196 days.

This patent is subject to a terminal disclaimer.

(21) Appl. No.: 11/424,405

(22) Filed: Jun. 15, 2006

(65) Prior Publication Data

US 2007/0293899 A1    Dec. 20, 2007

(51) Int. Cl.
A61N 1/00 (2006.01)
(52) U.S. Cl. .......................................... 607/9
(58) Field of Classification Search ............. 607/9, 607/14, 16
See application file for complete search history.

(56) References Cited

U.S. PATENT DOCUMENTS

| | | | |
|---|---|---|---|
| 3,057,356 A | 10/1962 | Greatbatch |
| 3,253,596 A | 5/1966 | Keller |
| 3,478,746 A | 11/1969 | Greatbatch |
| 3,595,242 A | 7/1971 | Berkovits |
| 3,648,707 A | 3/1972 | Greatbatch |
| 3,747,604 A | 7/1973 | Berkovits |
| 4,312,355 A | 1/1982 | Funke |
| 4,386,610 A | 6/1983 | Leckrone |
| 4,428,378 A | 1/1984 | Anderson et al. |
| 4,432,362 A | 2/1984 | Leckrone et al. |
| 4,476,868 A | 10/1984 | Thompson |
| 4,523,593 A | 6/1985 | Rueter et al. |
| 4,577,633 A | 3/1986 | Berkovits et al. |
| 4,587,970 A | 5/1986 | Holley et al. |
| 4,726,380 A | 2/1988 | Vollmann et al. |
| 4,727,877 A | 3/1988 | Kallok |
| 4,856,523 A | 8/1989 | Sholder et al. |
| 4,856,524 A | 8/1989 | Baker |
| 4,880,005 A | 11/1989 | Pless et al. |
| 4,890,617 A | 1/1990 | Markowitz et al. |
| 4,932,046 A | 6/1990 | Katz et al. |
| 4,941,471 A | 7/1990 | Mehra |
| 4,953,551 A | 9/1990 | Mehra et al. |
| 5,052,388 A | 10/1991 | Sivula et al. |
| 5,085,215 A | 2/1992 | Nappholz et al. |
| 5,097,832 A | 3/1992 | Buchanan |
| 5,117,824 A | 6/1992 | Keimel et al. |

(Continued)

FOREIGN PATENT DOCUMENTS

EP       0363015       4/1990

(Continued)

*Primary Examiner*—George Manuel
*Assistant Examiner*—Shubatra Narayanaswamy
(74) *Attorney, Agent, or Firm*—Stephen W. Bauer; Reed A. Duthler

(57) ABSTRACT

An implantable medical device includes cardiac pacing functions. In order to reduce ventricular pacing, various modes are employed that tolerate missed ventricular beats, provide backup pacing and maintain overall AV synchrony. Upon the occurrence of a PVC, A-A timing is modified so that resultant V-V intervals are appropriate and ventricular pacing is avoided.

20 Claims, 16 Drawing Sheets

U.S. PATENT DOCUMENTS

| | | | |
|---|---|---|---|
| 5,133,350 A * | 7/1992 | Duffin | 607/6 |
| 5,144,950 A | 9/1992 | Stoop et al. | |
| 5,163,427 A | 11/1992 | Keimel | |
| 5,188,105 A | 2/1993 | Keimel | |
| 5,188,117 A | 2/1993 | Steinhaus et al. | |
| 5,228,438 A | 7/1993 | Buchanan | |
| 5,273,035 A | 12/1993 | Markowitz et al. | |
| 5,292,340 A | 3/1994 | Crosby et al. | |
| 5,318,594 A | 6/1994 | Limousin et al. | |
| 5,334,220 A | 8/1994 | Sholder | |
| 5,345,362 A | 9/1994 | Winkler | |
| 5,372,607 A | 12/1994 | Stone et al. | |
| 5,388,586 A | 2/1995 | Lee et al. | |
| 5,417,714 A | 5/1995 | Levine et al. | |
| 5,522,859 A | 6/1996 | Stroebel et al. | |
| 5,540,725 A | 7/1996 | Bornzin et al. | |
| 5,584,868 A | 12/1996 | Salo et al. | |
| 5,591,214 A | 1/1997 | Lu | |
| 5,626,623 A | 5/1997 | Kieval et al. | |
| 5,643,326 A | 7/1997 | Weiner et al. | |
| 5,674,257 A | 10/1997 | Stroebel et al. | |
| 5,697,958 A | 12/1997 | Paul et al. | |
| 5,725,561 A | 3/1998 | Stroebel et al. | |
| 5,741,308 A | 4/1998 | Sholder et al. | |
| 5,814,077 A | 9/1998 | Levine et al. | |
| 5,836,974 A | 11/1998 | Christini et al. | |
| 5,861,007 A | 1/1999 | Hess et al. | |
| 5,861,012 A * | 1/1999 | Stroebel | 607/28 |
| 5,873,895 A | 2/1999 | Sholder et al. | |
| 5,954,755 A | 9/1999 | Casavant | |
| 5,999,850 A | 12/1999 | Dawson et al. | |
| 6,058,326 A | 5/2000 | Hess et al. | |
| 6,122,546 A | 9/2000 | Levine et al. | |
| 6,128,529 A | 10/2000 | Esler et al. | |
| 6,128,534 A | 10/2000 | Park et al. | |
| 6,141,586 A | 10/2000 | Mower | |
| 6,169,918 B1 | 1/2001 | Haefner et al. | |
| 6,198,968 B1 | 3/2001 | Prutchi et al. | |
| 6,256,541 B1 | 7/2001 | Heil et al. | |
| 6,321,115 B1 | 11/2001 | Mouchawar et al. | |
| 6,397,105 B1 | 5/2002 | Bouhour et al. | |
| 6,434,424 B1 | 8/2002 | Igel et al. | |
| 6,477,416 B1 | 11/2002 | Florio et al. | |
| 6,609,028 B2 | 8/2003 | Struble | |
| 6,654,637 B2 | 11/2003 | Rouw et al. | |
| 6,697,673 B1 | 2/2004 | Lu | |
| 6,731,980 B1 | 5/2004 | Mouchawar et al. | |
| 6,772,005 B2 | 8/2004 | Casavant et al. | |
| 6,792,307 B1 | 9/2004 | Levine et al. | |
| 6,873,875 B1 | 3/2005 | Gilkerson et al. | |
| 6,904,315 B2 | 6/2005 | Panken et al. | |
| 6,925,326 B1 | 8/2005 | Levine et al. | |
| 6,978,175 B1 | 12/2005 | Florio et al. | |
| 7,027,868 B2 | 4/2006 | Rueter et al. | |
| 7,123,960 B2 | 10/2006 | Ding et al. | |
| 7,130,683 B2 | 10/2006 | Casavant et al. | |
| 7,218,965 B2 | 5/2007 | Casavant et al. | |
| 7,245,966 B2 | 7/2007 | Betzold et al. | |
| 7,248,924 B2 | 7/2007 | Casavant et al. | |
| 7,254,441 B2 | 8/2007 | Stroebel | |
| 7,283,872 B2 | 10/2007 | Boute et al. | |
| 2002/0038482 A1 | 4/2002 | Mennicke et al. | |
| 2002/0041700 A1 | 4/2002 | Therbaud | |
| 2002/0082646 A1 | 6/2002 | Casavant et al. | |
| 2002/0128687 A1 | 9/2002 | Baker et al. | |
| 2002/0138417 A1 | 9/2002 | Lawrence | |
| 2003/0078627 A1 | 4/2003 | Casavant et al. | |
| 2004/0010292 A1 | 1/2004 | Amblard et al. | |
| 2004/0024694 A1 | 2/2004 | Lawrence et al. | |
| 2004/0078321 A1 | 4/2004 | Lawrence | |
| 2004/0117316 A1 | 6/2004 | Gillum | |
| 2004/0260349 A1 | 12/2004 | Stroebel | |
| 2005/0038482 A1 | 2/2005 | Yonce et al. | |
| 2005/0055059 A1 | 3/2005 | Betzold et al. | |
| 2005/0096708 A1 | 5/2005 | Seim et al. | |
| 2005/0177197 A1 | 8/2005 | Betzold | |
| 2005/0267539 A1 | 12/2005 | Betzold et al. | |
| 2005/0273430 A1 | 12/2005 | Pliha | |
| 2007/0203523 A1 | 8/2007 | Betzold | |
| 2007/0213777 A1 | 9/2007 | Betzold et al. | |

FOREIGN PATENT DOCUMENTS

| | | |
|---|---|---|
| EP | 0448193 | 9/1991 |
| EP | 0624386 | 11/1994 |
| EP | 0830877 | 3/1998 |
| EP | 1449562 | 8/2004 |
| WO | WO 95/32758 | 12/1995 |
| WO | WO 02/051499 | 7/2002 |
| WO | WO 2005/097259 | 10/2005 |
| WO | WO 2005/113065 | 12/2005 |
| WO | WO 2006/079037 | 7/2006 |
| WO | WO 2006/079066 | 7/2006 |

* cited by examiner

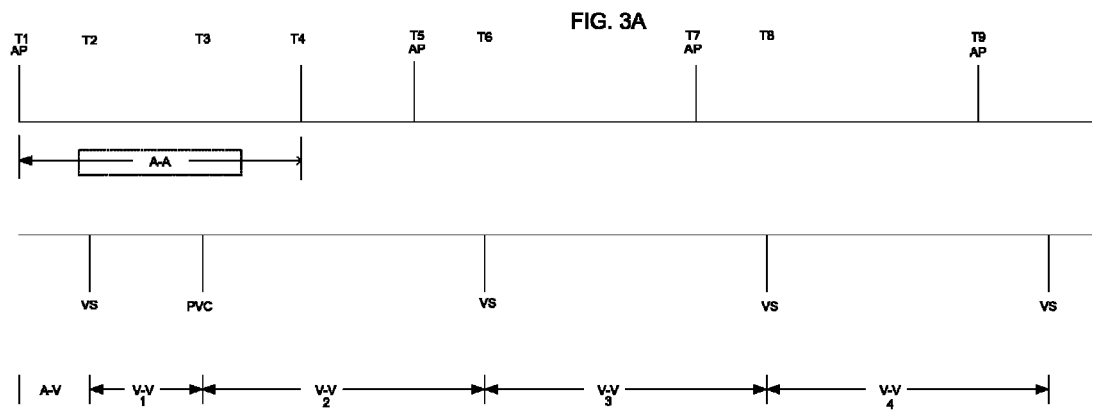
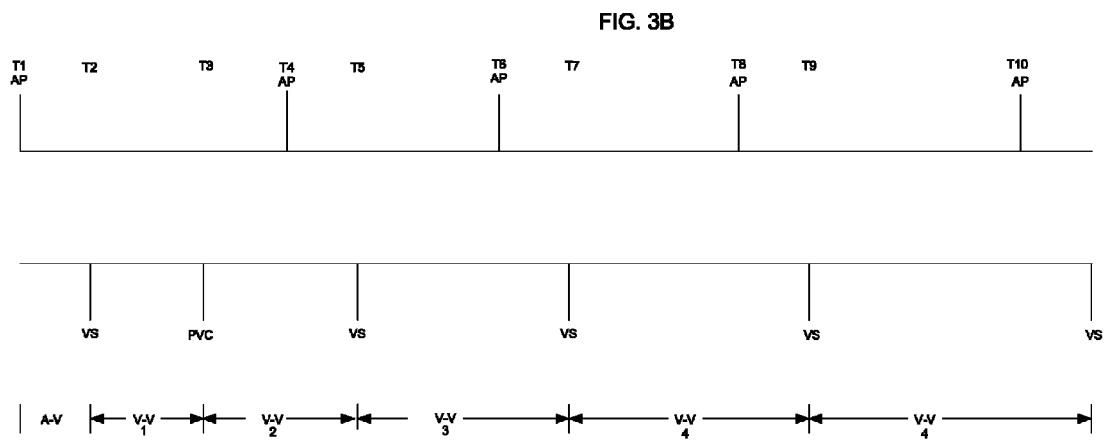

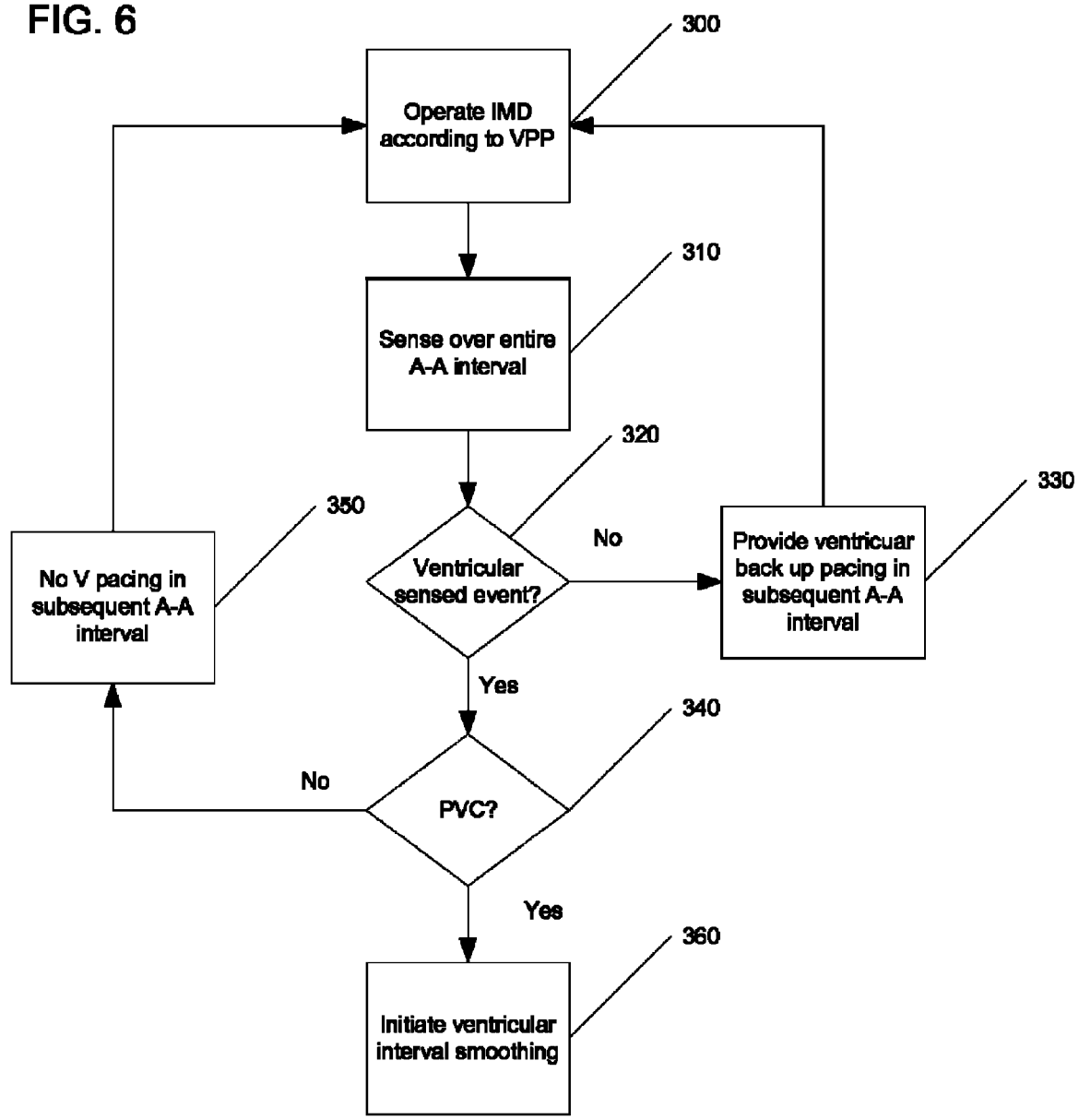

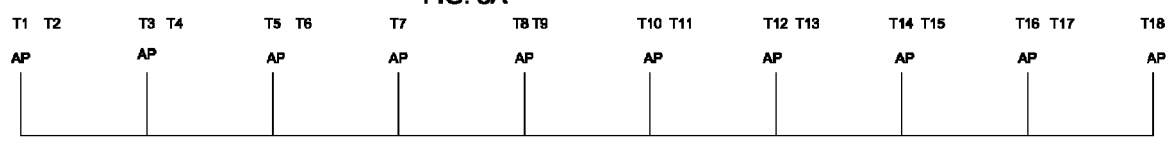
FIG. 8A
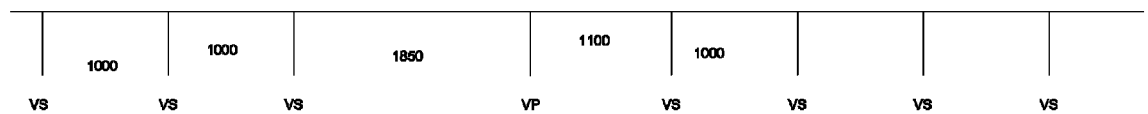
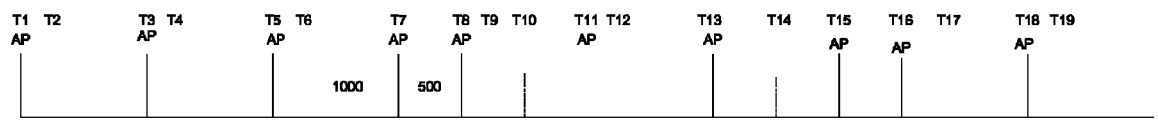
FIG. 8B
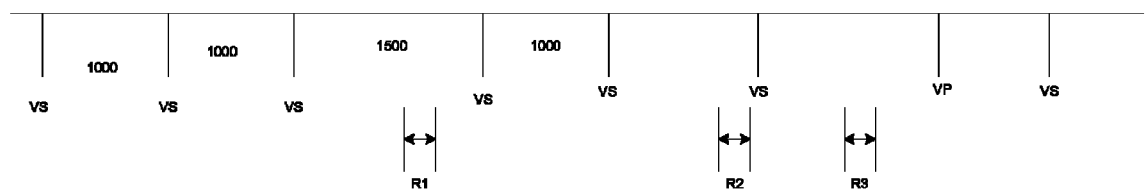

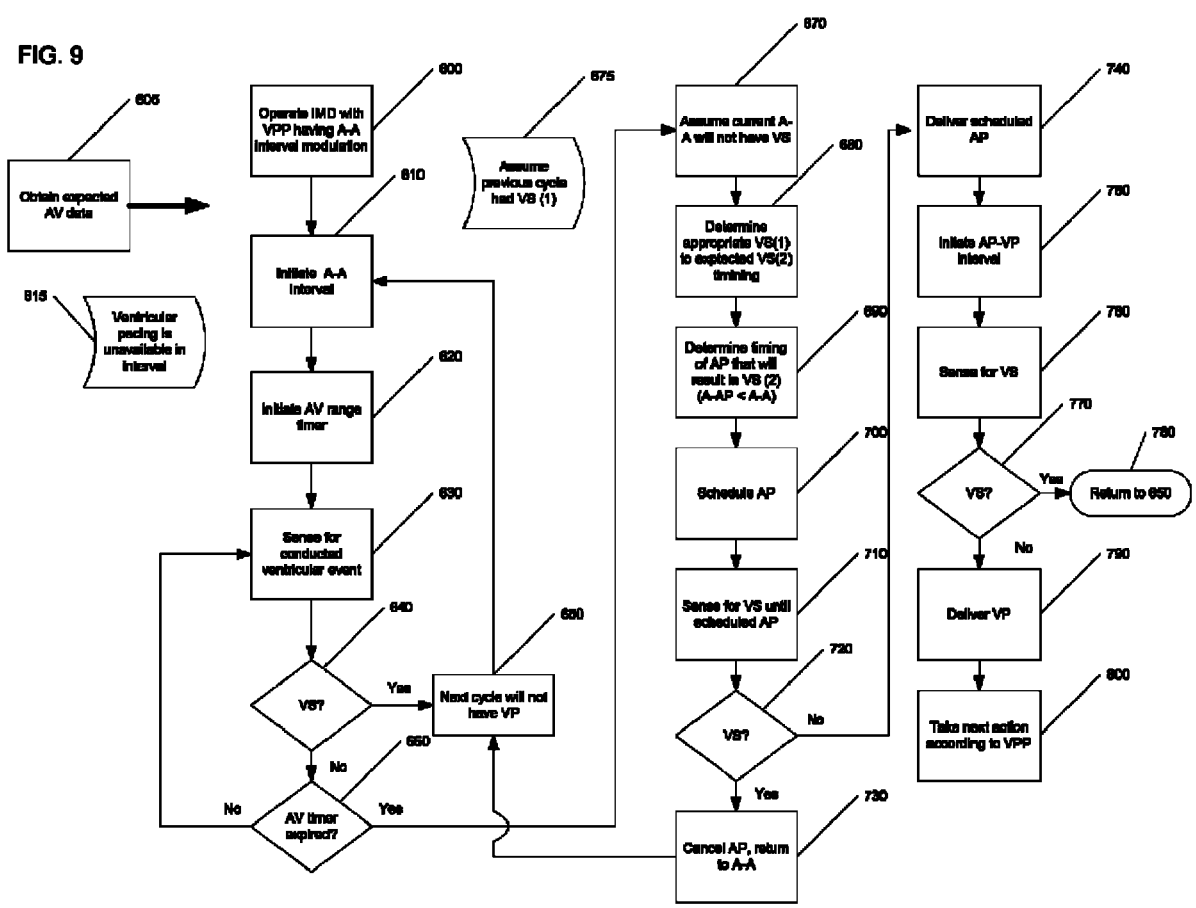

FIG. 12

| Atrial Rate (ms) | Conduction | AV Delay (ms) | Initial Testing/ RR | Progressive or Jump from LRI | Multiple confirmations ? | Percentage successful | Recent Success? |
|---|---|---|---|---|---|---|---|
| 1000 | Y | 275 | B | - | Y | 100 | Y |
| 975 | Y | 275 | B | P | Y | 100 | Y |
|  |  |  |  |  |  |  |  |
| 700 | Y | 290 | B | B | Y | 98 | 98 |
|  |  |  |  |  |  |  |  |
| 650 | Y | 295 | B | B | Y | 94 | N |
| 600 | Y | 295 | I | B | Y | 93 | N |
|  |  |  |  |  |  |  |  |
| 500 | Y | 300 | I | B | Y | 65 | N |
|  |  |  |  |  |  |  |  |
| 400 | N | - | I | J | Y | 0 | - |

SYSTEM AND METHOD FOR VENTRICULAR INTERVAL SMOOTHING FOLLOWING A PREMATURE VENTRICULAR CONTRACTION

FIELD OF THE INVENTION

The present invention relates to medical devices and more specifically to implantable medical devices.

DESCRIPTION OF THE RELATED ART

There are a variety of medical devices that sense data, provide diagnostic information, and/or deliver therapy. When such a device is implantable (in whole or in part), it is referred to as an implantable medical device (IMD). In the present application, "IMD" refers to devices that sense cardiac events and deliver pacing therapy. Such devices may or may not also include other functions such as defibrillation therapy (e.g., implantable cardioverter defibrillator (ICD)), other monitoring capabilities, alternate cardiac therapies, or non-cardiac monitoring and/or therapies. Thus, the term pacemaker may be used interchangeably with IMD in the present context with the understanding that either term may refer to a device with capabilities beyond those required of a pacemaker alone.

Recently, there has been a recognition that intrinsic conduction and ventricular depolarization, even if somewhat prolonged, is preferable to ventricular pacing; particularly pacing in or near the right ventricular apex. In general, this preference results from the unnatural propagation of a depolarization wavefront that is generated from such a pacing pulse (as compared to intrinsic depolarization).

Previous pacing modes tend to operate at one extreme or another. For example, in a true, single chamber AAI/R device, atrial pacing and sensing is possible, but no ability to provide ventricular pacing (or sensing) exists. On the other hand, DDD/R has historically been the default selection for dual chamber devices. The DDD/R mode will operate to maintain AV synchrony; however, the AV delay is necessarily such that intrinsic conduction is precluded in most cardiac cycles. This results in ventricular pacing in a very high percentage of cardiac cycles.

The present assignee has developed new modes that promote intrinsic conduction and are referred to herein generally as ventricular pacing protocols (VPP). One such VPP is Managed Ventricular Pacing™ (or MVP™) which is commercially available. A variety of VPP embodiments have previously been described, for example, as in U.S. Pat. No. 6,772,005, issued Aug. 3, 2004, to Casavant, et al., U.S. application Ser. No. 10/246,816, filed Sep. 17, 2002, U.S. application Ser. No. 10/755,454, filed Jan. 12, 2004, U.S. application Ser. No. 10/850,666, filed May 21, 2004, U.S. application Ser. No. 11/115,605, filed Apr. 27, 2005, U.S. application Ser. No. 11/096,436, filed Mar. 31, 2005, U.S. application Ser. No. 10/814,692, filed Mar. 31, 2004, U.S. application Ser. No. 11/364,290, filed Feb. 28, 2006, and U.S. application Ser. No. 10/971,686, filed Oct. 25, 2004, which are herein incorporated by reference in their entirety. Other related applications include U.S. application Ser. No. 11/258,523, filed Oct. 25, 2005, and U.S. application Ser. No. 11/257,643, filed Oct. 25, 2005.

As a generalized explanation, a VPP operates in an atrial based pacing mode to promote intrinsic conduction. Ventricular events are sensed and as long as a ventricular event is sensed in a given cardiac cycle (e.g., A-A interval) the device continues to operate in the atrial based pacing mode. This allows for ventricular sensing during the entire A-A interval. Conversely, if there is no ventricular event, the device provides a ventricular backup pace in the subsequent cycle, timed from the atrial event (paced or sensed) that initiates this subsequent cardiac cycle. Thus, in a VPP it is possible to have an entire cardiac cycle devoid of ventricular activity while ultimately maintaining AV synchrony. There are, of course, many variations and embodiments provided that are not described herein for the sake of brevity. It should be appreciated that operation in an atrial based pacing mode includes mode switching a device into such a mode (e.g. AAI/R, ADI/R) and into a mode that provides ventricular pacing (e.g., DDI/R, DDD/R, VVI/R, etc.) as necessary and potentially on a beat by beat basis or alternatively, operation in a complex mode that includes more comprehensive behavior (e.g., FIDDI) without necessitating mode switching to achieve the functionality described.

One benefit of a VPP is that the protocol may be initiated with patients regardless of the status of their AV conduction. Those having intact or partially intact conduction will benefit in that conduction is promoted and ventricular pacing is reduced or eliminated. For those patients with heart block, the VPP will quickly move to provide ventricular pacing and periodically check to determine if conduction has returned. Both in initially recognizing the need to pace and performing the conduction checks, the methodology employed is transparent to the patient.

As previously indicated physicians implanting a dual chamber device often utilize nominal settings and program the device to DDD/R due to its simplicity. The VPP allows for the same type of comprehensive reliability across patient profiles and without the need to program numerous parameters upon implant. The VPPs are preferable in that that they reduce or minimize ventricular pacing when intact conduction is present.

BRIEF DESCRIPTION OF THE DRAWINGS

FIGS. 3A-3C are timing diagrams illustrating operation according to various VPPs.

FIGS. 6-7 are flowcharts describing a method consistent with the teachings of the present invention.

FIGS. 8A-8B are timing diagrams illustrating operation according to various VPPs.

FIG. 9 is a flowchart describing a method consistent with the teachings of the present invention.

FIG. 12 is a sample data set of data collected from an atrial conduction test.

DETAILED DESCRIPTION

Figure 1:
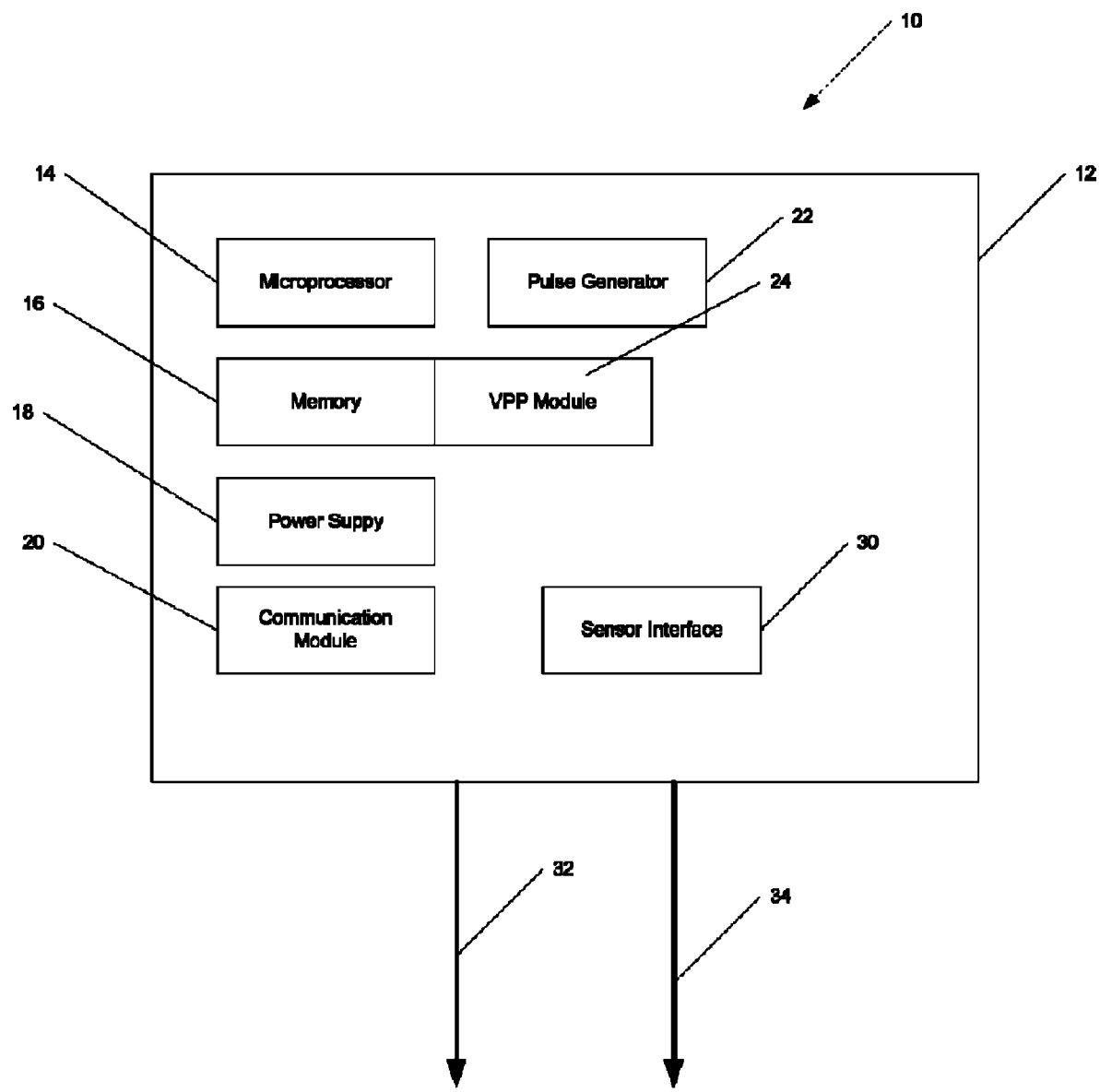
FIG. 1 is a schematic diagram illustrating an implantable medical device.

FIG. 1 is a schematic illustration of an implantable medical device (IMD) 10 having pacing capabilities. While not illustrated, IMD 10 may also include a variety of other monitoring, diagnostic and therapeutic functions. Further, FIG. 1 is not meant to comprehensively illustrate all components of an implantable pacemaker.

The IMD 10 includes a housing 12 that contains a microprocessor 14, memory 16, a power supply (e.g., battery) 18, a communication module 20 that facilitates telemetry to an external device and a pulse generator 22 for generating pacing pulses. A sensor interface 30 is provided to collect data from one or more sensors/electrodes, one or more of which may be disposed on leads 32, 34. The pacing stimuli generated by the pulse generator 22 is deliverable via the leads 32, 34. Also illustrated in FIG. 1 is a VPP module 24. It should be appreciated that these functions may be algorithms stored in the memory 16 or incorporated into other hardware, software, or firmware.

In operation, the IMD 10 senses cardiac events and provides an appropriate response. Most typically, cardiac events are sensed via electrodes on the leads 32, 34. These electrodes pick up electrical signals indicative of specific activities within the heart, typically represented as an electrogram (EGM) when generated from device data or an electrocardiogram (ECG) when based upon surface collected data. As is well known, the cardiac cycle includes an atrial depolarization represented electrically by a P wave, ventricular depolarization represented by the QRS complex, and repolarization represented by a T wave. While sensing algorithms can be relatively complex, in general a sensed P wave indicates intrinsic atrial depolarization while a sensed R wave indicates intrinsic ventricular depolarization. For a given pacing mode, if a P wave or R wave is not sensed within a predetermined time frame, then the IMD 10 provides atrial or ventricular pacing with appropriate timing, if supported by that mode. There are numerous variations to this generalization such as overdrive pacing or various tachycardia pacing therapies. The main point herein is that the IMD 10 senses data and responds in some fashion to that data.

Figure 2A:
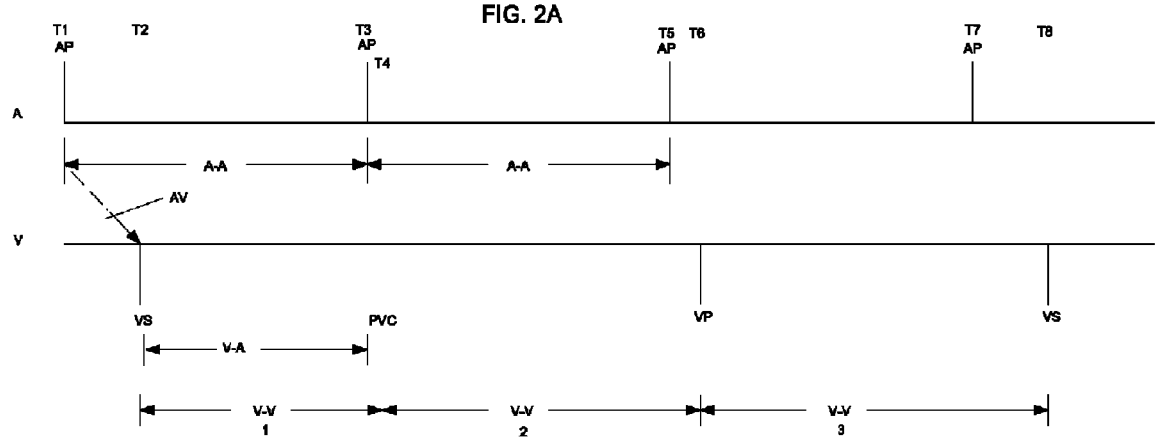
FIGS. 2A-2C are timing diagrams illustrating operation according to various VPPs.

As discussed, the present invention relates to an IMD 10 that selectively operates according to a VPP, such as for example, the MVP™ mode. There are many variations among the various VPPs and for the sake of clarity not every variation will be separately described. FIG. 2A illustrates a ladder diagram with sample timing data. The specific example relates to how a premature ventricular contraction (PVC) is addressed under one of the current VPPs; however, this diagram will also be used to explain the basic operation of a VPP.

The nomenclature presented will be consistently used throughout this description. In each diagram, the atrial channel (A) and ventricular channel (V) are illustrated. Events are indicated relative to one another according to time. In each example, atrial pacing (AP) is presumed with an A-A interval of 1000 ms. It should be appreciated that intrinsic atrial events (AS) may occur and are accounted for; however, they are not discussed in these examples. At time T1 an atrial pace (AP) is delivered. At time T2, the atrial event has conducted and intrinsic ventricular depolarization occurs (VS). The time between the AP and the VS is the AV delay. While the timing of the AP is known, the VS occurs naturally, thus, while expectations and averages may apply, the precise timing of the VS and the duration of the AV delay are not known until they occur. At time T3, the next AP is delivered; as indicated above the A-A interval is 1000 ms. The VA interval is the time from the VS to the AP (T3).

At time T4, a premature ventricular contraction (PVC) occurs. A PVC is any sensed ventricular event that is not triggered by a properly conducted atrial event or may be a properly conducted ventricular event resulting from a premature atrial contraction (which still leads to a ventricular event that is premature in overall timing). Thus, even though the PVC occurs after the AP at T4, it is effectively "too early" to be a proper ventricular event and is therefore considered a PVC. Nonetheless, the PVC is a ventricular event/ventricular depolarization. As such, the time from the VS to the PVC is referred to herein as the first V-V interval (V-V (1)). With the caveat that intrinsic ventricular events may vary, if the A-A interval is steady at 1000 ms the V-V interval (absent PVC's, conduction block, or other abnormalities) should also be approximately 1000 ms. Another type of PVC may also occur and would Departing from the example for a moment, if the illustrated PVC were a properly conducted VS (i.e., occurring later in the cycle), then V-V (1) would likely have been about 1000 ms. The next AP would occur as illustrated at time T5; followed most likely by an intrinsic ventricular event rather than the illustrated VP. In other words, this is how the VPP would work if events were normal. In general, any sensed ventricular event occurring during any portion of a given A-A interval satisfies the criteria to continue normal operation. The exception to this is a PVC as will be explained in detail. Only when a complete cycle (A-A interval) is devoid of proper ventricular sensed events, will the next cycle include ventricular pacing.

In this example, the PVC occurs during a defined crosstalk window. That is, a period of time following the AP where sensed ventricular events are effectively ignored (at least the first such occurrence). Thus, for purposes of the VPP, the PVC at time T4 is ignored and is effectively equivalent to not having a sensed a ventricular event occurring in the A-A interval between times T3 and T5. As such, the response of the VPP is the same in either instance (no V event or early PVC). That is, the A-A interval (T3-T5) is deemed devoid of ventricular activity. Thus, in the next A-A interval (T5-T7), a ventricular "backup" pace (VP) is delivered at time T6. In this example, in the cycle beginning with the AP at time T7, conduction returns and the VS occurs at time T8. If conduction had not returned, various options are available based upon the specific VPP embodiment. Such options would include, for example, conduction checks, and operation in a dual chamber pacing mode for various amounts of time.

Returning to the specific example illustrated, when the PVC occurs and is ignored under the current VPP, certain issues arise. That is, although the PVC is ignored as a ventricular event, it does depolarize the ventricles, although at a less than optimal time and with less than an optimal contraction. Again, in normal timing, V-V intervals (in this example) should be approximately 1000 ms. Here, because of the PVC, the V-V timing is 1000 ms in the cycle prior to T1 (not illustrated), 800 ms for V-V(1), 1050 ms for V-V(2), and then about 1000 ms for V-V(3). This sequence is normal, short, long, normal. Furthermore, the long duration (or "pause" as used herein) following the short duration is terminated with a ventricular pacing pulse. While this mode of operation is generally appropriate, there is some belief that this type of pattern, particularly when terminated with a ventricular pace may be proarrhythmic in a small patient population. This theory is widely disputed and its validity is not known. However, the present invention provides mechanisms to minimize this scenario if there is in fact validity to the concern.

Figure 2B:
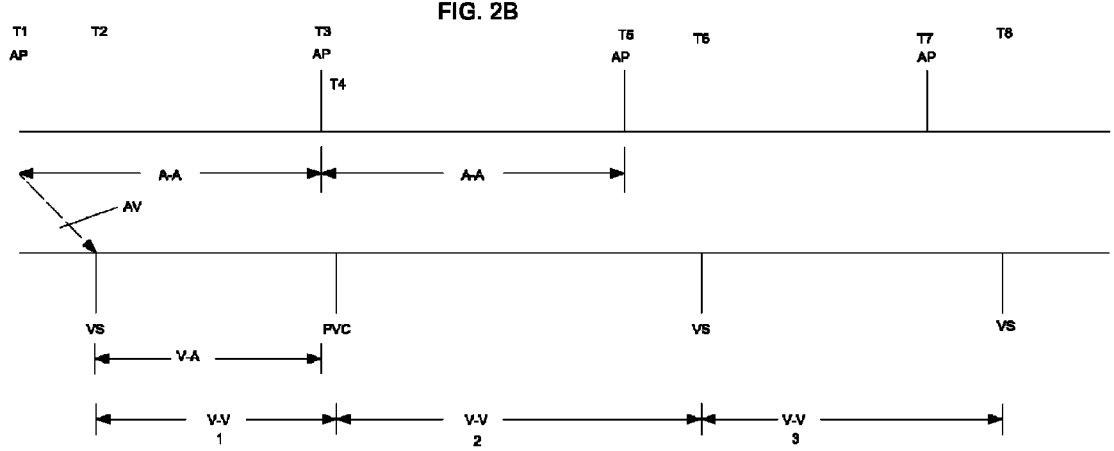

In a first embodiment of the present invention, illustrated in FIG. 2B, the timing of the events is substantially the same as that of FIG. 2A. The distinction here is that the PVC, despite occurring in the crosstalk window is considered as a ventricular event; thus, a ventricular pace is not provided in the next cycle (T5). Rather, intrinsic conduction occurs and a VS is noted at time T6. The V-V variation is approximately the same (1000 ms, 800 ms (V-V (1)), 1200 ms (V-V (2)), 1000 ms (V-V (3))); however, the long pause is not terminated with a ventricular pace. Rather, intrinsic conduction is permitted; thus, reducing the disruptive effects that might result from pacing in such a situation for certain patients. If the VS had not occurred at time T6 and none occurred at all in the A-A interval (T5-T7), then a ventricular pace would have been delivered following the AP at T7. To summarize, in this embodiment the acceleration in ventricular timing (800 ms), followed by a deceleration (1200 ms) is terminated by an intrinsic event as opposed to a ventricular paced event.

Figure 2C:
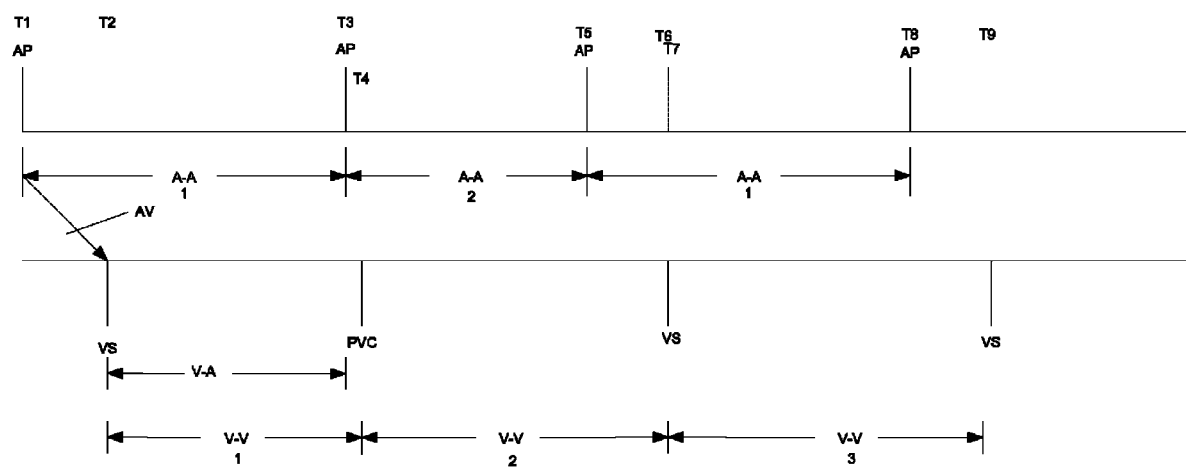

FIG. 2C represent another embodiment referred to as a VPP with ventricular rate stabilization (VRS) or rate smoothing. In dual chamber modes, (e.g., DDD/R) VRS address the same type of acceleration/deceleration in V-V timing generated by PVCs. However, in a dual chamber mode, ventricular pacing is almost always provided and certainly always available. Thus, the AV interval and the VA interval are completely controlled and in response to a PVC, these intervals are varied to gradually return to a normal timing pattern. With the VPP, there is no control over ventricular timing; thus, this approach is impossible.

At time T1, the AP is delivered and a VS occurs at time T2. An A-A interval of 1000 ms expires and the next AP is delivered at T3. As in the previous examples, a PVC occurs (during the crosstalk window) at time T4. To ultimately affect the V-V timing, the A-A interval is modified. Thus, after the PVC the current A-A interval is truncated and an AP is delivered "early" at time T5. In this example, the shortened A-A interval is about 750 ms. As an example, the VS has generally been occurring about 250 ms after the AP in this "patient". Thus, at time T6 the VS occurs. By chance, this happens to approximately align with the previously scheduled 1000 ms AP (which does not occur) at time T7. It should be appreciated that these two times may or may not correspond. Another AP is delivered at time T8 with a normal VS at time T9. The result is that the prior V-V interval (not shown) is about 1000 ms, V-V (1) is about 800 ms (PVC is an early event, hence some acceleration of V-V timing); V-V (2) is about 950 ms (because of the early AP and resulting VS); and V-V (3) returns to the normal 1000 ms interval. The resultant V-V intervals are substantially "smoother;" that is, their durations are relatively similar and large accelerations and large decelerations are avoided. Once the A-A interval is shortened, this approach allows a smoother, more gradual return to normal timing rather than a one cycle jump. In addition, the ventricular event occurring between times T5 and T8 is intrinsic, which as described above is preferable to relying upon ventricular pacing. More atrial cycles could be relied upon to effectuate the smoothing, with each resultant V-V interval varying by a smaller amount; thus, while taking longer to return to a given value an even smoother transition is provided. The number of cycles and the delta between consecutive intervals may be selected to provide the desired degree of "smoothing."

Thus, this embodiment controls A-A timing to effectuate variations in V-V timing without providing ventricular pacing. As such, this embodiment represents a VPP having a ventricular rate stabilization or smoothing effect.

There are several factors to consider within the scope of the present invention in varying A-A intervals to effectuate V-V timing. The "early" AP must not be too early so as to pace when the atrium is refractory and/or similarly result in a conducted event occurring when the ventricles are refractory. Furthermore, the amount of the adjustment is based upon known or expected AV timing (which as explained, is not controlled by the device). In other words, the desired effect is to achieve an intrinsic ventricular depolarization at or about time T6 (in this example). Thus, the IMD 10 determines the likely AV time that will result, and shortens the A-A interval by this amount.

FIG. 3A is an example of how the prior VPP(s) would treat a PVC occurring approximately 400 ms after a properly sensed ventricular event and within the same A-A interval. Again, the example assumes atrial pacing in every cycle with an A-A interval of 1000 ms. Thus, the A-A interval previous to the first illustrated (referred to as A-A (0)) was 1000 ms in duration, with a VS at about 250 ms and no PVC occurred.

At time T1, the AP is delivered and an interval of 1000 ms is started. At time T2, a VS occurs (about 250 ms). A PVC occurs at time T3, which is about 400 ms after the VS and thus about 650 ms into the cycle. The notation at time T4 indicates when the next AP was scheduled to be delivered (e.g., at the termination of the 1000 ms interval). In general, the way that the previous VPPs treated a PVC occurring after a VS was to add an interval or in other words delay the subsequent AP. This effectively means that a VA interval is initiated at the PVC (T3). The value of this interval may be varied; in this example a value of 920 ms is utilized (current A-A interval (1000 ms)−80 ms (where 80 ms is the AV interval for a backup V pace). As such, an AP is delivered at time T5 and a normal VS occurs at time T6, with the pattern normalizing through time T9.

The result is a 1000 ms V-V (0), a 400 ms V-V (1), an 1150 ms V-V (2), and 1000 ms interval for V-V (3) & (4). Thus, a long pause (1150 ms vs. 400 ms) occurs in V-V timing. In this instance, the pause is terminated by a VS. In another scenario, no VS occurs during the A-A interval defined by time T5 to T7. This would result in a VP occurring proximate time T8, thereby extending V-V (2) to about 2000 ms. Thus, the pause is longer and is terminated by a pacing pulse.

FIG. 3B illustrates an embodiment of the present invention that smoothes the V-V intervals in response to the same PVC occurring at 400 ms by controlling A-A timing. Again, an AP occurs at time T1 (initiating a 1000 ms interval) followed by a VS at time T2. A PVC occurs at time T3. The current VPP embodiment attempts to have the V-V intervals be relatively smooth, progressively larger, and gradually return to the appropriate value (e.g., 1000 ms in this case). Thus, V-V (1) establishes the initial interval at 400 ms. The IMD 10 determines what V-V (2) interval should be, based upon the value of V-V (1). Based upon what this value is (550 ms in this example), the desired timing of the VS at T5 is determined. Since the IMD 10 cannot control when the VS will actually occur, it calculates what the likely AV delay will be, subtracts this interval from the time T5 and provides an atrial pace at this time (T4); contrasted with the example of FIG. 3A where a long VA (920 ms) is added to the PVC before the next AP. The interval (VA) between T3 and T4 must be appropriate and non-refractory. Furthermore, the IMD 10 (based upon patient historical data) determines that this VA is not likely to lead to conduction block.

The AP is delivered at time T4 and the VS occurs at time T5 (about 250 ms later in this example). As indicated, V-V (2) is about 550 ms and a subsequent jump to 1000 ms would be too large a delta; thus, the above process is repeated. A desired V-V value is determined; the necessary timing of the VS is determined, the likely AV value is subtracted, and the AP is delivered at that time. Here, the AP is delivered at T6 and V-V (3) is 700 ms. The same process is repeated again and the next AP is delivered at time T8 with a resultant V-V(4) of about 850 ms. Finally, the AP at T9 returns the V-V interval to the initial rate of 1000 ms. Correspondingly, the A-A interval from T4-T6 is 700 ms, T6-T8 is 850 ms, and from T8-T9 is 1000 ms. Thus, by varying the A-A intervals using the VPP smoothing function, the resulting intrinsic ventricular timing may be influenced and the resultant V-V intervals adjusted to avoid large deltas between sequential cycles without actually pacing the ventricles.

If an AP is scheduled following a PVC and another PVC occurs prior to delivery of that AP, several options exist. First, the IMD 10 determines if the timing of the second or subsequent PVC would still permit the scheduled AP to be delivered in an effective manner. If so, the AP is delivered. If not, then a standard delay may be added to the AP timing (e.g., delay by 400 ms); the delay may be set to the duration of the interval between PVC's; or the above process is repeated in its entirety as the V-V intervals (may) have been changed by the occurrence of a subsequent PVC.

It should be readily appreciated that the examples used herein are for illustrative purposes only. The numerical values selected merely aid illustration and are in no way limiting. The specific values that would be chosen would vary depending upon patient specific criteria.

Figure 3C:
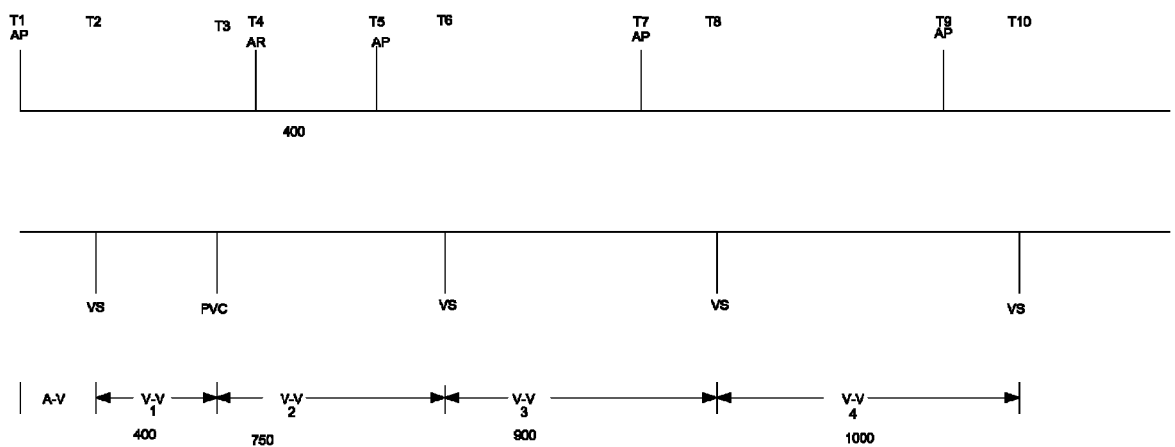

FIG. 3C illustrates how the above embodiment would respond to an atrial refractory event. Comparison is made between FIGS. 3B and 3C. At time T3 (in each figure), the PVC occurs. At time T4 (FIG. 3C), an atrial refractory event (AR) occurs thus prematurely depolarizing the atrium. Of course, if conducted the ventricles are refractory so this does not affect ventricular depolarization. If the AP were delivered at the same time it was in FIG. 3B, the atrium would be refractory and would not depolarize. Thus, despite the desire to smooth the V-V variability, the AP must be delayed because of the AR. In this example, the AP is delayed 400 ms from the AR. The delay may be a determination of atrial repolarization or some surrogate such as A-V intervals (averaged, median, etc.) for a given rate, or an A-V value plus an offset such as 50 ms to assure reliability. The AP is delivered at time T5 and the VS occurs at time T6. The process then continues as previously described. In this case, V-V (1) is still 400 ms, V-V (2) is 750 ms, which is greater than 550 ms of FIG. 3B but still significantly shorter than the 1100 ms of FIG. 3A, V-V (3) is 900 ms and V-V (4) returns to 1000 ms. Thus, an atrial refractory event causes a somewhat longer pause, but the present embodiment is still able to smooth V-V intervals by adjusting A-A timing and avoids ventricular pacing.

Figure 4A:
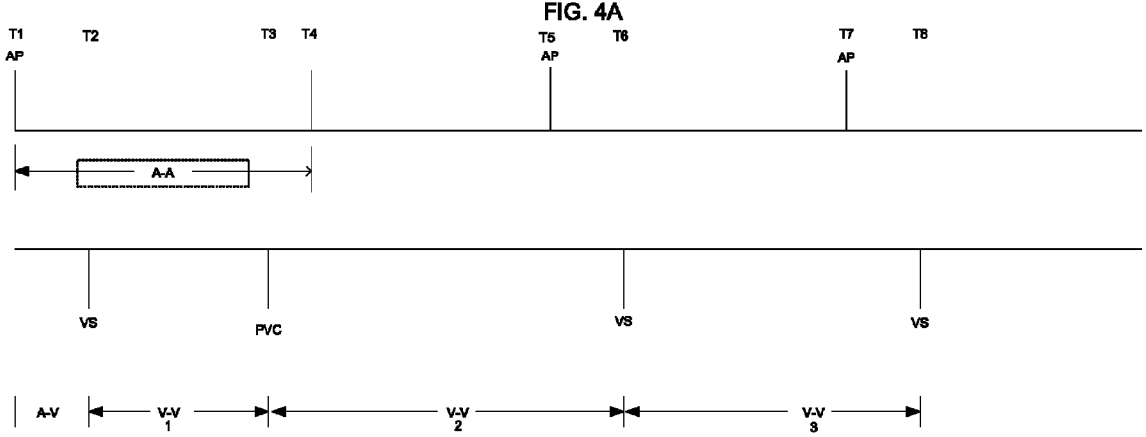
FIGS. 4A-4C are timing diagrams illustrating operation according to various VPPs.
Figure 4B:
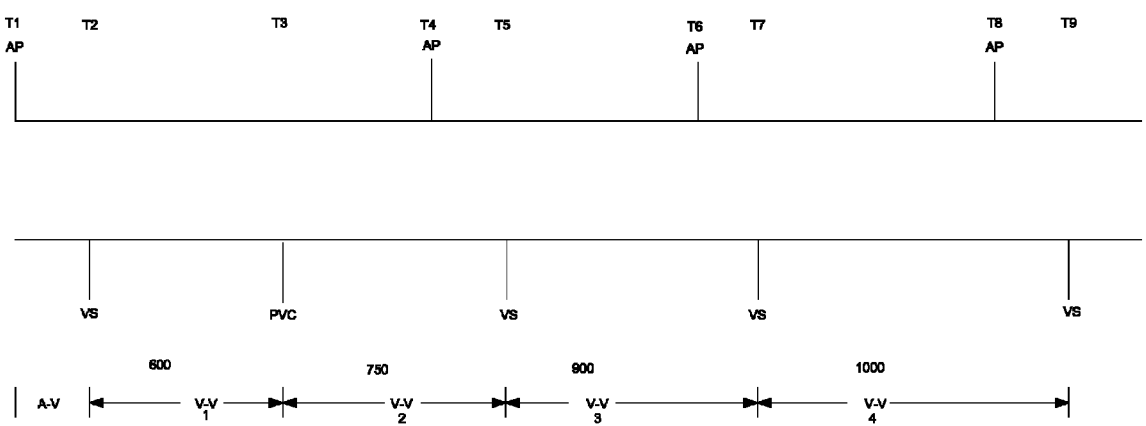
Figure 4C:
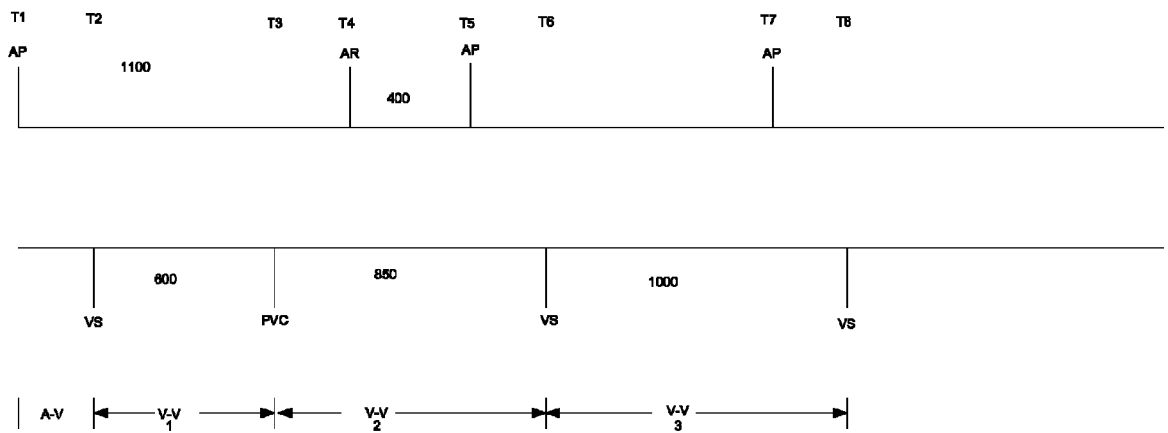

FIGS. 4A-4C are substantially similar to FIG. 3A-3C, however the PVC occurs 600 ms after the VS, rather than 400 ms. The resulting processes are the same and the V-V intervals, in this example are as follow:

FIG. 4A Previous VPP(s)
V-V(1) 600 ms
V-V(2) 1200 ms
V-V(3) 1000 ms
FIG. 4B Present Embodiment
V-V(1) 600 ms
V-V(2) 750 ms
V-V(3) 900 ms
V-V(4) 1000 ms
FIG. 4C Atrial Refractory event
V-V(1) 600 ms
V-V(2) 850 ms
V-V(3) 1000 ms In certain embodiments of the present invention, the A-A intervals are adjusted during VPP operation so that resultant V-V intervals are influenced, without providing ventricular pacing (as a general rule). The determination of values may be based on various criteria. For example, once a given (short) V-V interval occurs (e.g., due to a PVC), the next V-V interval (and each thereafter until the desired rate is achieved) may be increased by some predetermined percentage such as 10, 15, 20, 25, 30, 35, 40 or 45 percent. Alternatively, a predetermined value may be added to the subsequent V-V interval (and each thereafter until the desire rate is achieved) such as for example 50, 100, 150, 200 or 250 ms.

Thus, the desired V-V interval is selected. To implement this interval, the A-A interval is calculated accordingly and the atrial pace is delivered at an appropriate time. The determining factor is the AP to VS time value (AV delay or interval). In other words, the desired time for a VS to occur is selected and the AV delay is subtracted to determine when to pace. The present invention provides various mechanisms to determine this likely AV delay.

In one embodiment, the AV delay times are recorded by the IMD 10 over some period of time. This may be for the overall implant life or some subset such as the last 12 hours, the previous 100 cardiac cycles or other predetermined period of time. The AV delay is averaged or a median AV value is determined and utilized. By using a statistically significant but relatively short time line, the median AV delay, for example, is more likely to be accurate than over the lifetime of the implant. For example, the median over the previous 100 cardiac cycles would account for the patient's current condition and status.

Figure 5A:
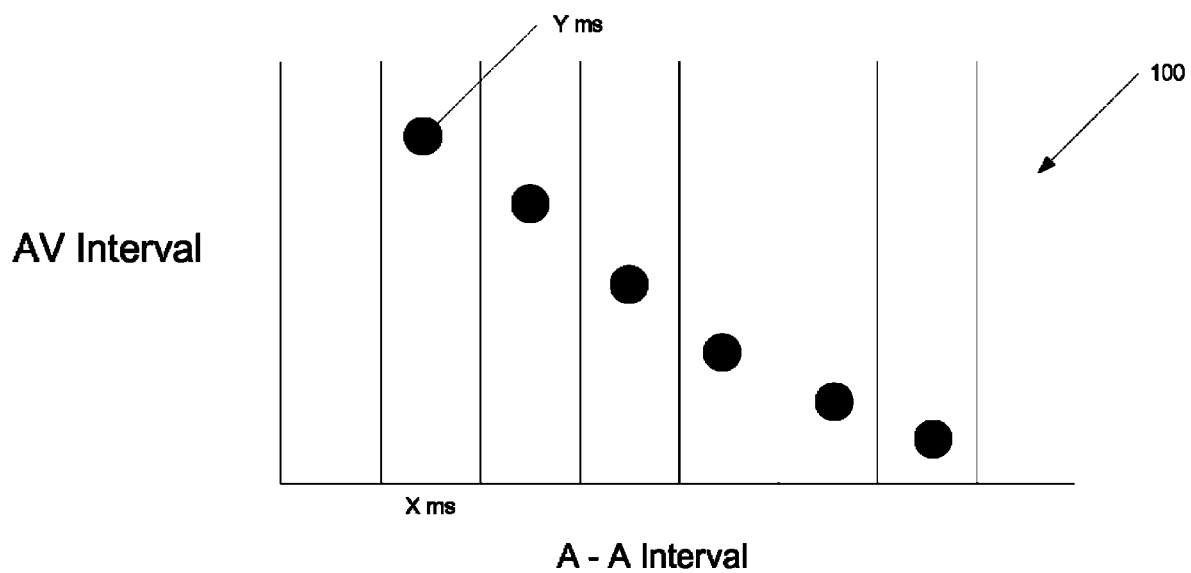
FIGS. 5A and 5B illustrate a conduction delay table and graph.

In another embodiment, a table of AV delays is kept for various A-A intervals. Such a table 100 is illustrated in FIG. 5A. A given data point may represent one of several potential items. A data point may simply indicate what an AV delay for a given A-A interval is, based upon patient experience. Alternatively, the data point may be an averaged value, median, etc. of AV delays for the same A-A delay. Finally, the data point may represent the shortest successful AV delay for a given A-A interval. This may be a single event or alternatively, a plurality of successful conductions at this delay may be required prior to entry into the table. The table is meant to indicate at least what AV delays are likely to succeed (i.e., conduct successfully) at a given A-A interval and to the extent the data is available, the shortest tolerable AV delay for any given A-A interval.

The table provides various discrete data points, from which other data may be extrapolated. That is, if the above methodology requires an A-A interval of a given duration to smooth V-V intervals and that A-A interval has no data in the table, the likely AV delay may be extrapolated.

Figure 5B:
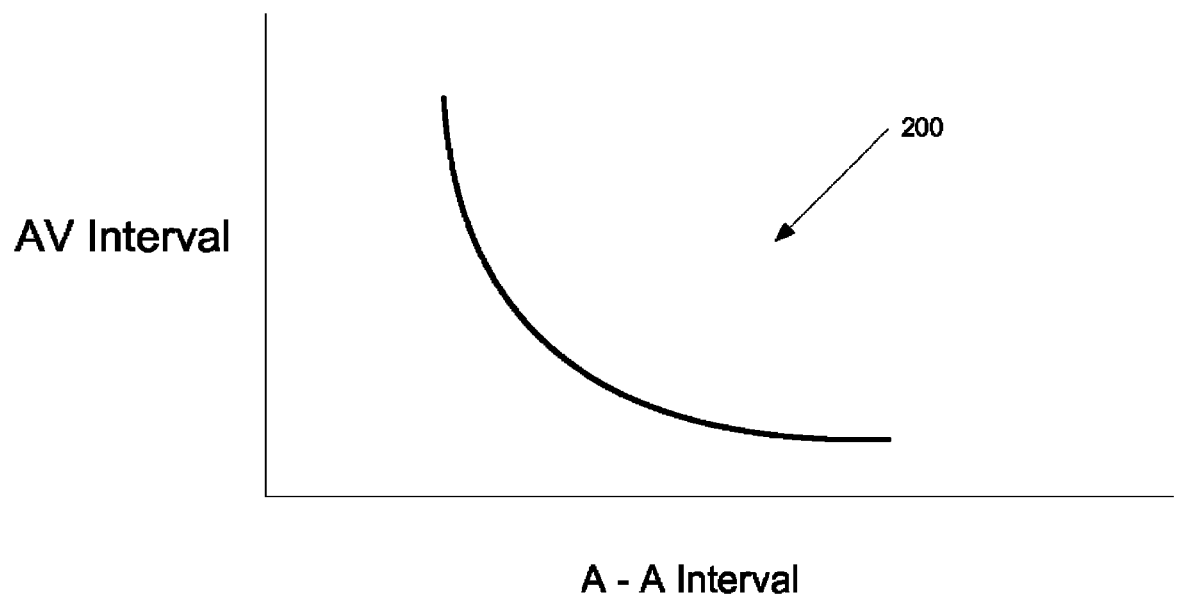

In another embodiment, the extrapolation of data takes into account the non-linear relationship between A-A intervals and AV delay. In reality, the AV delay can only be truncated so much (successfully) regardless of how short the duration of desired A-A interval. Choosing between relatively long A-A intervals (e.g., 1100 ms vs. 1000 ms) has different tolerances than relatively short A-A interval (e.g., 400 ms) variations. Thus, FIG. 5B illustrates a sample graph 200 where a non-linear component is added to an extrapolation of the data obtained from e.g., the table 100 of FIG. 5A. This margin increases the likelihood that a selected A-A interval will result in a conducted event. It is generally preferable to err on the side of providing a longer A-A interval (resulting in a longer V-V interval) than to try to have too short an A-A interval that fails to conduct.

In another embodiment, a decision is made to smooth V-V intervals. A calculation is performed to determine what A-A interval is required to effectuate the desired V-V interval. The IMD 10 then determines whether this A-A interval will successfully conduct (that is, actual data supports the interval and its requirements). If so, then the A-A interval is utilized. If not, then a ventricular pacing pulse is provided to ensure the desired V-V interval. This embodiment is the least preferred, and distinct from the others, for the above stated reason that ventricular pacing is always less preferable to conduction. Generally, it would likely be more preferable to revert to the prior VPP (e.g., FIG. 2A). However, the present invention provides for a variety of embodiments so that various options may be provided to clinicians who may then select the most appropriate VPP for their patient.

Figure 7:
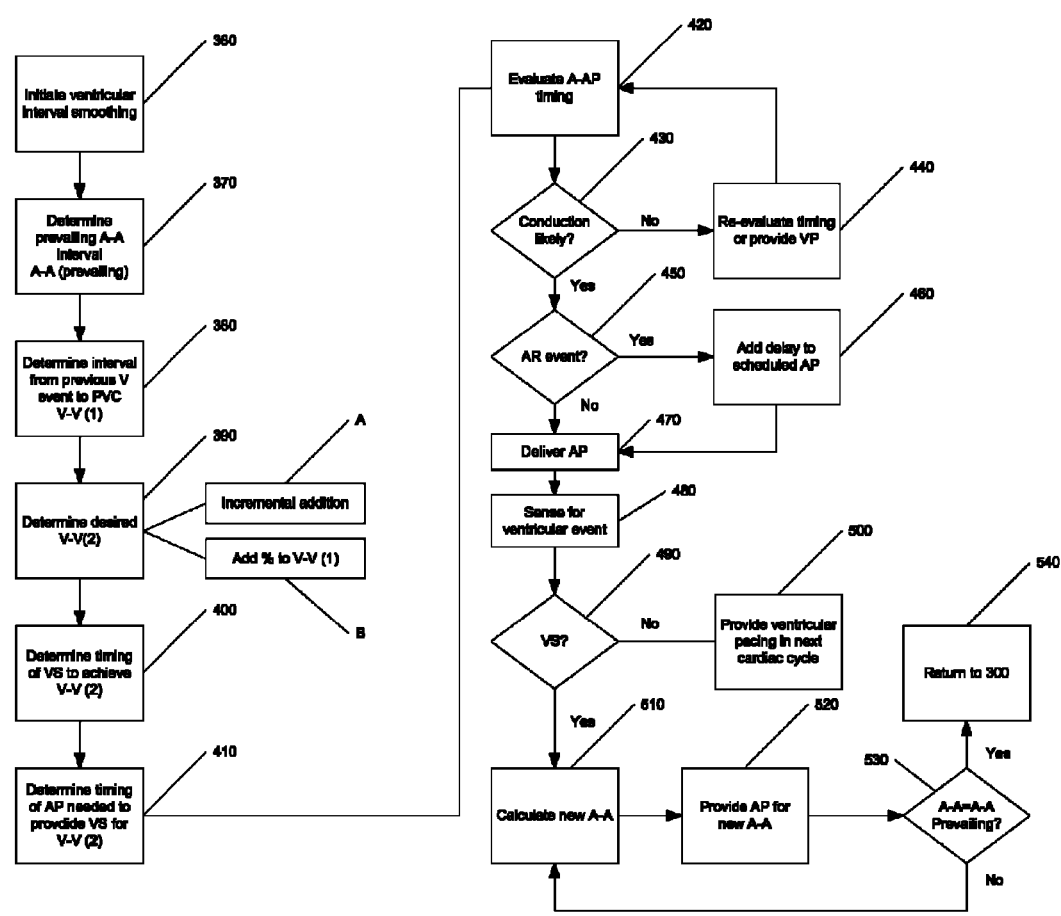

FIGS. 6-7 are flowcharts that present the methodology of various embodiments consistent with the teachings of the present invention. The IMD 10 is programmed to operate (300) according to a VPP (ventricular pacing protocol) such as, for example, the MVP™ mode. As a general summary, the VPP operates by freely providing atrial pacing as desired and of course, relying upon intrinsic atrial depolarization whenever appropriate. Ventricular pacing is generally withheld and a full cardiac cycle (A-A interval) is permitted to lapse without ventricular activity. If a cycle lapses without ventricular activity, then a ventricular backup pace is provided in the next subsequent cycle, appropriately timed from the atrial event. The next action(s) taken will vary based upon the embodiment of the VPP. For example, in the following cycle (after a ventricular pace) ventricular pacing may be withheld again to allow for intrinisic conduction. If this pattern is repeated a certain number of times, a mode switch to a dual chamber mode (e.g., DDD/R) is made for some predetermined amount of time. This generalized description addresses normal operation of the VPP when proper ventricular events are sensed and/or no ventricular event is sensed.

Returning to the flowchart, this process is described. An entire A-A interval (whether defined by atrial pacing at some rate and/or intrinsic atrial depolarization) is monitored (310); that is, the ventricles are sensed for ventricular depolarization in response to a conducted atrial event. It should be appreciated that various blanking periods are still utilized during a given A-A interval and should not lead to confusion regarding monitoring over the "entire" A-A interval.

During the A-A interval, the ventricular channel is monitored for conducted events. If no (320) ventricular event is sensed, then a ventricular pacing pulse is provided (330) in the subsequent A-A interval. After that, the process returns and continues to operate according the parameters of the VPP. Conversely, if a ventricular event is sensed (320) a determination is made as to whether this event is a PVC (340). It should be appreciated that during this monitored A-A interval, a first sensed ventricular event may be classified as a PVC if it occurs so early in the cycle that it would not have resulted from conduction. Conversely, a proper ventricular event may be sensed and then a second ventricular event within the same A-A interval may also be sensed. This second (or subsequent) event would be classified as the PVC (340).

If no PVC is detected (340), then the IMD 10 will operate (350) in the next subsequent A-A interval as it has in this interval. That is, no ventricular pacing is provided and the entire A-A interval is monitored. Thus, the process returns to normal VPP operation (300).

If a PVC (340) is detected, then the VPP initiates (360) the ventricular interval smoothing function, which is illustrated in FIG. 7. While the process is described in a particular sequence, it should be appreciated this order is non-limiting and that various actions may occur in a different sequence and/or simultaneously. Furthermore, while various actions are called out for explanatory purposes, there may not be any specific action taken as the result is the gathering of a known variable or value (e.g., determining A-A intervals—this value is typically "known" to the IMD 10).

The IMD 10 determines (370) what the prevailing A-A interval is at the time of the PVC. If atrial pacing has been prevalent, this is simply the escape interval for the atrial pacing component, which will likely (but not necessarily) be rate responsive. In the above examples, this was 1000 ms for illustrative purposes. If the atrial rhythm was intrinsic, then the AS-AS intervals were sensed by the IMD 10 and while not controlled by the device, the timing was known.

The IMD 10 then determines (380) a value for V-V(1) which is the time from the previous ventricular event to the PVC. In order for the event to be a PVC it must have either occurred too early in the cycle and absent the present methodology, the next V-V interval would be too long (and likely terminated by a VP); or the PVC occurs after the VS and therefore introduces a very short V-V interval which would be followed by a long V-V interval. Therefore, the IMD 10 determines (390) what the appropriate value for V-V(2) should be based upon the value of V-V(1) and the A-A prevailing rate. That is, the objective is to return to the V-V prevailing rate in a smoother or gradual, stepped fashion and avoid large variances.

The IMD 10 may utilize various methodologies in calculating V-V (2). As illustrated, one example (A) is to add some incremental value to the V-V (1) interval. This may be a standard value (e.g., 50 ms, 100 ms, etc.) or may be a value linked with the value of V-V (1). For example, if V-V (1) is particularly short (200 ms) adding 50 ms may result in an unworkable V-V (2). Therefore, there may be a minimum allowable V-V (2) value. Thus, while various options are available the result is that some value is added to V-V (1) to arrive at V-V (2). In the other example (B), V-V (2) is created by increasing V-V (1) by some percentage (e.g., 10, 15, 20, 25, 30, 35, 40%, etc.), with the same caveats relating to the V-V(2) value being too short and therefore extended to a predetermined minimum.

Once the value for V-V (2) is determined, the IMD 10 determines when an AP would need to be delivered so that intrinsic conduction would lead to a VS at the appropriate time. Thus, steps 400 and 410 are effectively coincident as determining the AP timing necessitates knowing the expected AP-VS timing and vice versa.

The IMD 10 evaluates (420) whether the A-AP timing is likely to permit/facilitate conduction (430). If not, then the timing is reevaluated (440) or as indicated for one embodiment, ventricular pacing is provided. In order to evaluate the likelihood of conduction, various methods may be utilized. In one embodiment a table of known AV delays is provided and either utilized or a value is extrapolated if no corresponding data point is present. In another embodiment, average or median AV delays are stored and this value is utilized. In another embodiment, a patient specific table is created (as above), and a non-linear modifier is utilized for extrapolation to account for the non-linear correspondence between A-A intervals and AV delays over the spectrum of possible A-A intervals. Finally, another embodiment is to utilize a given value if the IMD 10 "knows" (based on stored data) that conduction will very likely occur and to provide ventricular pacing if this confidence in a specific value is unavailable Assuming the timing of the AP and the expected V-V (2) are satisfactory and would reasonably lead to a conducted ventricular event, the AP is scheduled. During the interim, the atrial channel is monitored for refractory events. If an AR occurs (450), then a predetermined delay value (e.g., 400 ms) is added to delay the AP until the atrium is repolarized.

At the appropriate time, the AP is delivered (470) and the ventricular channel is sensed (480) for a VS. If the VS does not occur, then ventricular pacing is provided in the subsequent cycle according to the normal operation of the VPP. Assuming the VS does occur (490), the next A-A interval (and V-V (3)) is calculated (510) (using the described methodology) and the appropriately timed AP is delivered (520). That is, V-V (3) is longer than V-V (2), and each interval progresses toward the desired duration.

The current A-A interval (and effectively V-V interval) are compared (530) to the prevailing A-A interval. If they are the same or very close, then the process is complete and operation returns to normal according to the VPP parameters (300). If the A-A interval is not substantially equal to the prevailing (or desired) A-A interval, the process returns to step 510 and another incremental V-V value is generated. This process is repeated as often as necessary to return to the desired rate. In the examples previously described, this would take 2-3 cycles; however, this is non-limiting.

FIG. 8A is a timing diagram again illustrating basic operation with one existing embodiment of a VPP. Atrial events are paced and the A-A interval is 1000 ms, in this example. Similarly, the VS-VS intervals are also 1000 ms. At time T5 an AP is delivered that is followed by a VS at time T6. At time T7, the next AP is delivered (1000 ms after T5). Because of the VS at T6, no ventricular pacing will be provided in the A-A interval between T7 and T8. As illustrated, no ventricular event is sensed in this interval. The AP is delivered as scheduled at time T8 and a ventricular pace VP is delivered at time T9, in this example about 100 ms after the AP. The next AP is delivered 1000 ms after the last, at time T10 and a VS occurs at time T11. The VS events are illustrated as occurring about 250 ms after the AP.

The result of this pattern is that when conduction is present the V-V interval is about 1000 ms. The VS-VP interval is about 1850 ms, the VP-VS interval is about 1100 ms (due to relatively short AP-VP interval, which is deliberate), and the next VS-VS is again 1000 ms. This is normal operation and no PVCs or other extraneous events are present. Operation in this manner is well tolerated by the patient population and results in a dramatic reduction in ventricular pacing for patients having some degree of intact conduction. That said, even absent a PVC there is a pause that is terminated with a ventricular pace.

FIG. 8B illustrates a new embodiment of a VPP according to the present invention that may be used in and of itself as well as in combination with the above ventricular interval smoothing functions. At T5 the AP occurs, followed by the expected VS at T6. At T7, the next AP is delivered. One of the basic principles of the VPP mode is that ventricular pacing is precluded in a cycle following a cycle were ventricular activity was sensed. That said, there is no requirement that a given A-A interval have any specified value; intrinsic atrial events could always inhibit a scheduled AP. Thus, the present embodiment utilizes the ability to "control" or rather influence intrinsic ventricular events through the timing of atrial pacing.

Following the AP at time T7, there is some expected time during which a VS is likely to occur and this range is illustrated as range R1. This is patient specific and based upon history (or demographical data when specific patient data is insufficient or unavailable). Thus, the range R1 could provide for an AV delay that is much longer than what would typically occur for dual chamber pacing modes. Nonetheless, even with patients having prolonged conduction, there is generally some predictability. If no VS occurs by the end of the range R1, then the timing of next AP is advanced or accelerated so that a VS is likely to occur at time T9. Time T10 indicates when the originally scheduled AP would have occurred. The same calculation methodology previously described may be used herein.

The A-A interval between T7 and T8 is truncated and devoid of ventricular activity. As a practical matter, had the AP not been advanced this cycle would most likely still be devoid of a VS. Now, in the cycle from T8-T11, ventricular pacing is available, but the PAV (paced AV) interval is not set to the short (80-100 ms) duration as previously used. Rather, sufficient time is given that intrinsic conduction leads to the VS at time T9. In considering resultant V-V intervals, there is still a pause (though shorter than in FIG. 8A); however, it is terminated with an intrinsic ventricular event rather than a ventricular pace. For intermittent dropped beats, this is the most likely result; that is, if given an opportunity intrinsic conduction will likely reemerge after a single skipped cycle.

The next AP is delivered at T11 (1000 ms after the early AP at T8). At T13 an AP is delivered and no VS occurs during the expected range R2. Thus, the IMD 10 schedules an early AP to occur at about time T14. In this example, a VS occurs after the expiration of the range R2, but prior to delivering the early AP. Thus, the early AP is cancelled and the originally scheduled AP is delivered at time T15.

As illustrated no VS occurs between T15 and T16 (a shortened A-A similar to T7-T8). Thus, with the delivery of the AP at T16 it is hoped that a VS will occur as previously described. There may be block or other issues and no VS occurs within the set PAV interval. As such, a VP is delivered at T17. This simply illustrates that after a truncated A-A devoid of ventricular activity, the next cycle will have ventricular activity; either through an intrinsic event that is given a better chance to emerge due to the early AP and delayed VP, or if necessary by the VP. It should be appreciated that these events are illustrative and that no correlation is meant to be indicated by the proximity of events having missed beats; they are proximate simply for illustrative convenience and are otherwise unrelated. One could assume that numerous cycles elapsed between the described cycles having accelerated atrial pacing. The VPP may take certain action based upon patterns emerging over a number of cycles and the present embodiment does not exclude such action and merely presents various possible scenarios in proximity for ease of illustration.

FIG. 9 is a flowchart illustrating a VPP using A-A interval modulation to reduce the occurrence of providing ventricular pacing following a skipped ventricular beat while controlling V-V intervals. The IMD 10 begins operation (600) according to the VPP of the present embodiment. Over time, the IMD 10 will record data (605) indicative of the patient's AV delays at various A-A intervals. Until that patient specific data has been recorded, preprogrammed AV data may be utilized as a surrogate. For purposes of this example, we assume that some number of previous A-A intervals (whether paced or not) have had successful ventricular conduction. Thus, the initiation of the A-A interval (610) simply represents a cardiac cycle following a cycle where a conducted ventricular event occurred. Once again, the A-A interval may be paced or entirely intrinsic and an assumption of consistency due to rate is made for illustrative purposes only.

This A-A interval begins and an AV range timer is initiated (620). This timer represents when, for this rate, this patient will likely have a conducted ventricular depolarization. The timer is referred to as a range timer as some margin may be added to the expected timing to account for normal and/or tolerable variations. As a VS occurred in the previous cycle, ventricular pacing will not (615) be available in this cycle. The ventricular channel is sensed (630) for a conducted event. The IMD 10 determines if a VS has occurred (640), if a VS occurs then the next cardiac cycle will also be precluded from having ventricular pacing (650) and the process returns to 610 for the next A-A interval. If no VS occurs (640), the IMD 10 evaluates the status of the timer (660) and continues to monitor until the timer's expiration.

If the timer expires without a VS occurring, then the protocol "assumes" that no VS will likely occur in the current A-A interval (670). Ventricular pacing is precluded as previously indicated. The IMD 10 evaluates (680) the timing of the previous VS and what an appropriate V-V interval would be, assuming a skipped event in this interval. Next, a calculation is made as to when an AP would need to be delivered (early, as compared to the expected A-A interval) that would likely conduct and result in a VS as this time (690). While described as separate steps, it should be appreciated that these calculations are related. That is, the current rate, the likelihood of atrial capture, and the likelihood of conduction leading to a VS, as well as the resulting V-V interval are all utilized in the determination.

Once the timing has been calculated, this early AP is scheduled (700). Until that time, the ventricular channel continues to be monitored (710) and if a VS (720) occurs, the early AP is cancelled (730) and the process returns to step 650. In other words, the VS occurred outside of the AV range timer but within the original A-A interval; thus, that interval is considered as having a conducted ventricular event and the process proceeds accordingly.

Assuming that no VS occurs prior to the scheduled delivery, the early AP is delivered (740). In the A-A interval initiated by this AP, ventricular pacing is available as the previous (truncated) cycle was devoid of a ventricular event. In other VPP embodiments, the VP is delivered rather quickly post AP (e.g., 80 ms); in the present embodiment, the AP was timed so that assuming normal conduction (preferably specific to this patient), a VS is likely to occur at an appropriate time. Therefore, an AP-VP interval is initiated (750) wherein upon expiration a VP will be delivered, unless inhibited by a VS. The AP-VP interval is selected so that the VP is scheduled after the expected VS (optionally plus some margin). In most cases, a VS will occur but in those rare instances where it does not, ventricular pacing is provided.

As indicated, the ventricular channel is monitored (760) for a VS during the AP-VP interval. If a VS occurs (770), then the VP is inhibited and the process returns to step 650 as this cycle is has a conducted ventricular event. As previously discussed, the resulting V-V interval is somewhat longer than the preceding V-V intervals; however, this pause is terminated by an intrinsic ventricular event rather than a paced event. If no VS occurs (770), then the scheduled VP is delivered (790) and the next steps are taken (800) according to the specific VPP.

Through the new embodiments discussed above, various VPPs have been provided that alter atrial timing in order to effect a change in ventricular intervals. These VPPs allow for intrinsic conduction to occur over an entire A-A interval and only if that interval is devoid of a ventricular sensed event will ventricular pacing be provided in the next cardiac cycle. This modification of atrial timing may be made in any cycle where it appears unlikely that a ventricular event will conduct and/or in situations where a PVC will create anomalous intervals. It should be appreciated that by utilizing these embodiments, various arrhythmias are likely avoided. As a consequence, the need to deliver cardioversion or defibrillation shocks is reduced.

In general, patients tolerate one skipped ventricular beat well; however, a ventricular event (paced/sensed) will occur in the cycle subsequent to the skipped beat. Absent the above described atrial timing modifications, the existing VPP may result in a V-V interval equal in duration to twice the lower rate minus the PAV (assuming normal/consistent AP-VS durations). Ventricular timing is not controlled in this manner; this is simply the numerical result. Referring to FIG. 8A, the VP at time T9 is scheduled to be delivered at the end of a PAV that is initiated with the AP at time T8. Thus, the timing of this VP is not related to the previous VS but in retrospect, the interval between these two events may be measured. To be completely accurate, the maximum duration (assuming fixed A-A intervals at the LRI) is twice the atrial lower rate interval (LRI) plus the AP-VP interval minus the AP-VS interval (2*LRI+(APVP)–(APVS)). As indicated, in various circumstances it may be desirable to shorten this interval and/or end the interval with an intrinsic event rather than a paced event. Thus, the A-A intervals are varied to achieve these effects.

As discussed, modifying atrial timing will likely result in conducted events occurring at a desired time. In order to make this more likely, A-A intervals may be selected based upon patient data that indicates previous successful conduction at that interval. Despite this, the possibility remains that an accelerated atrial event will initiate a cycle where conduction does not occur and a ventricular pace is delivered. Thus, there are two factors in consideration. The first is the likelihood of successful conduction at a given atrial rate. The second is the resultant VS to VP interval, when ventricular pacing is required. These two factors will define the boundaries of the permissible atrial acceleration as well as the PAV that is set.

Figure 10:
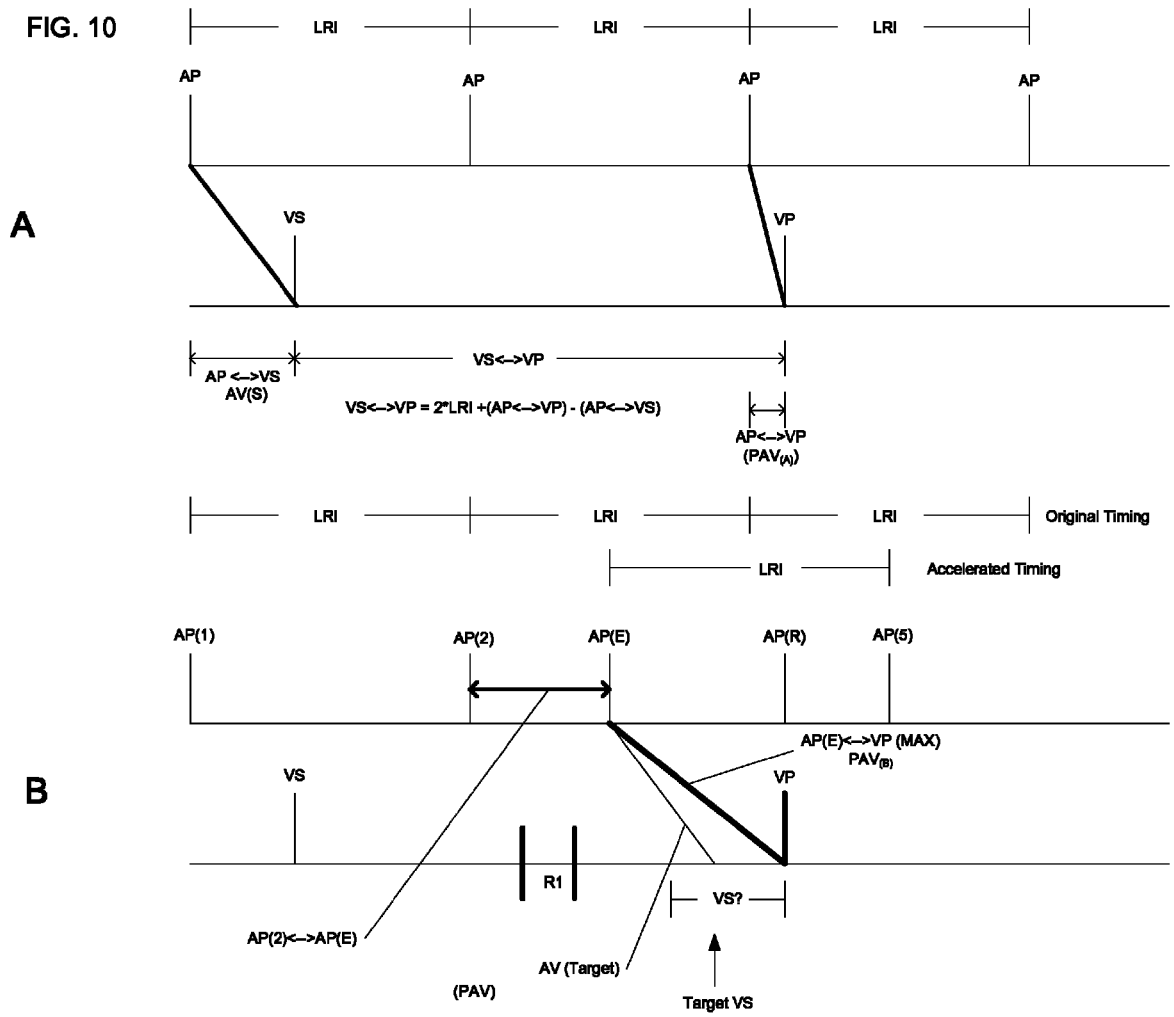
FIG. 10 is a timing diagram illustrating boundary conditions for one embodiment.

Referring to FIG. 10, portions of two timing diagrams are illustrated. Timeline A illustrates the prior VPP with a maximum V-V interval, in one scenario. It should be appreciated that the illustrated timing of the VS is arbitrary and if it had occurred earlier in the cycle, the resulting V-V interval would be longer. Thus, "maximum" is relative in the sense that the actual AP-VS timing may vary, the A-A interval may vary, and a different PAV may be set. However, the relationship defined by the variables, regardless of their specific values in a given example, does in fact establish the relevant reference points.

In this example, the IMD 10 is providing atrial pacing at the lower rate interval (LRI). An atrial AP is delivered, followed by a ventricular sensed event (VS). At the end of the A-A interval, a second AP is delivered and no ventricular event occurs. A third AP is delivered and the $PAV_A$ (e.g., 80 ms) is initiated. At the end of the $PAV_A$, a ventricular pace (VP) is delivered. In practice, a VA interval (not illustrated separately) begins and upon expiration, the fourth AP is delivered (at the same time the LRI would have expired). This diagram simply illustrates normal operation upon skipping a ventricular beat for this VPP.

Assuming the A-A interval is set to the LRI, the illustrated VS to VP interval is a retrospective maximum, relative to the timing of the VS. As indicated, VS to VP may be defined as:

$$V\text{-}V_{(max)} = 2*\text{LRI} + \text{PAV}_{(A)} - AV(S)$$

Thus, in some of the embodiments that seek to accelerate atrial timing this may be used as the maximum V-V interval tolerated. As indicated, V-V timing is not controlled directly. Another metric similarly defining a boundary condition, again referring to FIG. 8A, is the AP(7) to AP(8) interval plus the PAV (AP–VP). This would equal the lower rate interval plus, e.g., 80 ms.

Referring to timeline B in FIG. 10, the progression is the same as timeline A through the delivery of the second atrial pace AP(2). As previously described, a range R1 is provided that establishes the expected timing of a conducted ventricular event. As illustrated, no such event occurs and the range interval R1 expires. As such, an accelerated atrial pace AP(E) is scheduled. As previously explained, a desired timing for an VS to occur (Target VS) is determined; the AV delay (target) is determined, and from this the timing of the AP(E) is calculated. The AP(2)–AP(E) interval is evaluated to determine if conduction is likely to occur in this patient; if so, the timing is utilized and if not, then the values are reevaluated. Upon delivery of the AP(E), a $PAV_{(B)}$ is initiated; upon expiration a ventricular pacing pulse VP will be delivered unless inhibited by a VS. Assuming the VP is delivered, an optional AP(R) may be delivered simultaneously or at approximately the same time. This prevents retrograde conduction into the atria from affecting the efficacy of the next AP(5). As illustrated, the delivery of the VP in timeline B corresponds to the delivery of the VP in timeline A and is therefore the maximum acceptable in this embodiment. As such, timing parameters that result in the VP being delivered as illustrated in timeline B or sooner are generally appropriate.

With this understanding, certain relationships may be established for the variables. The use of the ↔ indicates the interval between the two items.

| AP(2) ↔ AP(E) | ≧ AP(2) ↔ R1 (expiration); and |
| --- | --- |
| | ≦ LRI; and |
| | ≧ shortest known A-A w/ conduction (optional) (where known A – VS ≦ AP(E) – VP) |
| $PAV_{(B)}$ | ≦ LRI – (AP(2) ↔ AP(E)) + $PAV_{(A)}$; and |
| | ≧ AP(E) ↔ Target VS |
| | ↓ $PAV_{(B)}$ ↓ VS-VP |
| | ↑ $PAV_{(B)}$ ↑ VS Opportunity |

That is, the shorter the $PAV_{(B)}$, the shorter the VS-VP interval. Conversely, the longer the $PAV_{(B)}$, the greater the opportunity to allow a conducted event; that is more time is provided for conduction to occur. It should be appreciated that the usage of these values/rules as boundary conditions is not a requirement of the present invention, and may be selectively utilized in various embodiments.

In a given patient, there may be multiple cardiac cycles where the range timer R1 expires and an accelerated atrial pace (AP(E)) occurs. As indicated, this will typically result in an appropriately timed ventricular sensed event. However, if it does not the ventricular pace will be delivered. If a ventricular pace is delivered under this scenario multiple times, then a decision may be made to forego the above described $PAV_{(B)}$ or more accurately to shorten it so that a ventricular pace is delivered as the desired target VS time. That is, if it becomes apparent that intrinsic ventricular conduction will fail under these conditions based upon past attempts, then there is still benefit in accelerating the atrial timing and providing ventricular pacing to smooth the V-V intervals. The number of attempts that should be made prior to taking this action may be selected by the caregiver. As general guideline, sufficient attempts should be made to establish whether intrinsic conduction will emerge when accelerated atrial pacing is utilized. In an extremely conservative setting, one failed attempt may be utilized as a basis to accelerate atrial pacing and provide ventricular pacing to achieve the smoothing interval. Alternatively, more attempts may be made such as 5, 10, 20, 100, etc., before changing the approach. Of course, this numbers are merely exemplary and are non-limiting. As another variable, the number of failed attempts may be cumulative over time and a successful attempt may restart the count. Alternatively, having a high number of failures with a minimal number of successful attempts may also change the pattern. Finally, the timing of the failed attempts may increase or decrease the relevance on the decision. That is, if a number of attempts have failed and there has been a long interval (e.g., days) without a skipped interval, the algorithm may attempt to promote intrinsic conduction and accelerate the atrial interval despite the number of previously failed attempts as the patient's status may have changed in the interim. All of these variables may be programmed by the caregiver, set to default values, or may be disabled.

As previously noted, a desired timing for a sensed ventricular event is calculated. The appropriate AV delay is subtracted to determine when to deliver the accelerated atrial pace (AP (E)). The AP-AP(E) interval is evaluated to determine whether this is feasible. Of course, this is merely exemplary and the ordering or steps taken may vary. In some embodiments, whether or not to attempt the accelerated timing is based upon data if available, extrapolations of available data, generalized patient demographic data, or device determination (i.e., trial and error).

In other embodiments, the decision whether to accelerate atrial pacing and the specific A-A interval chosen is made only if patient specific data is available and/or if the extrapolation required is highly probable. One way of collecting data is by making observations at different atrial rates implemented when the device is in a rate responsive mode. While data obtained in this manner is perfectly acceptable, several issues exist. First, at the time of an event requiring this determination, the patient may not have experienced an atrial rate (due to rate responsiveness) or one sufficiently close to provide relevant data. Second, many patients will not have the rate response function enabled. For example, certain heart failure patients may simply rely on atrial pacing at the LRI. For those patients, there is never an ability to collect data at the varying atrial rate (absent intrinsic atrial rate changes).

Figure 11:
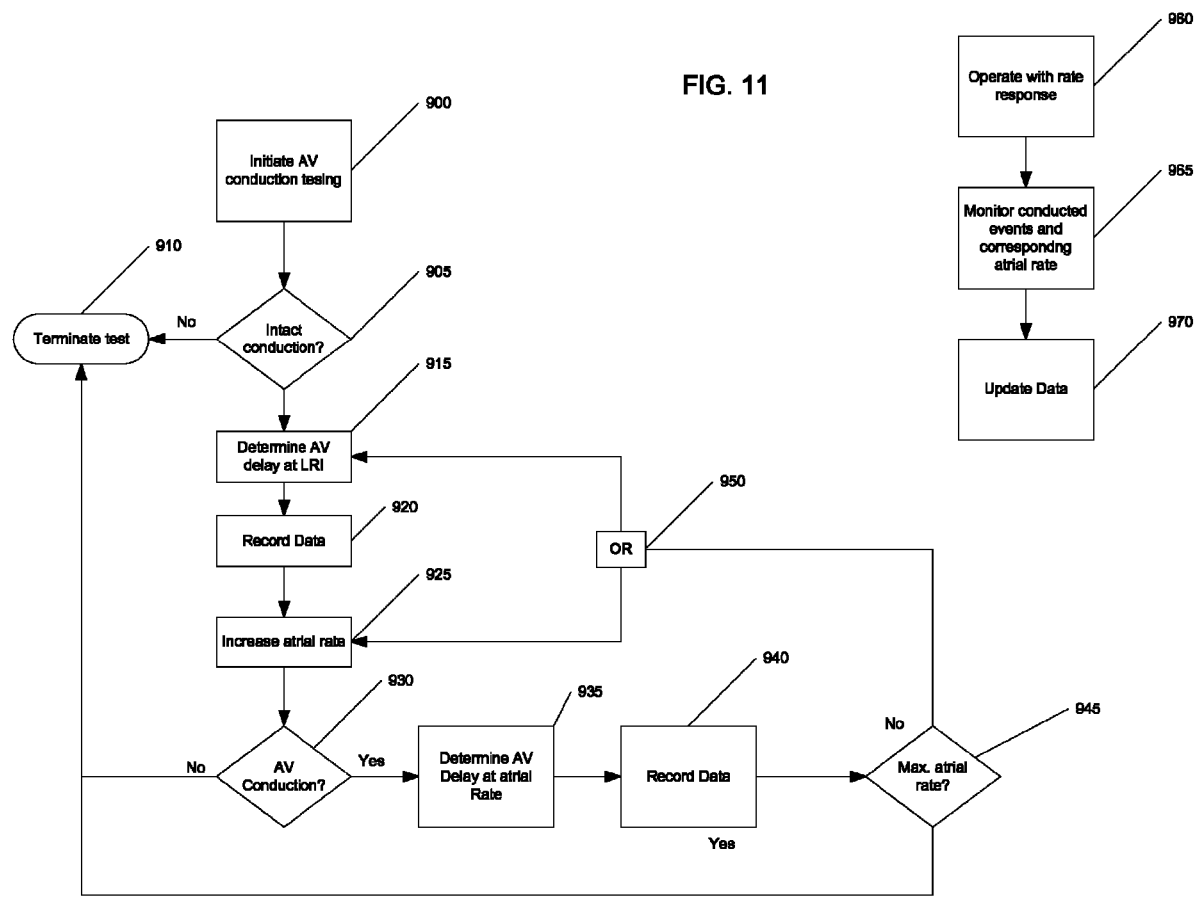
FIG. 11 is a flowchart describing a process for conducting an atrial conduction test according to one embodiment.

FIG. 11 is a flowchart describing one process for collecting data so that patient specific data is available for the calculations. The process is referred to herein as AV conduction testing and would be performed by a clinician at implant and/or during selected follow up appointments. The IMD 10 may also automate some or all of this testing and perform the testing on a periodic basis; likewise, such testing may be done via remote programming, assuming appropriate safeguards are in place.

The AV conduction testing is initiated (900) and the first issue is to determine if the patient has intact conduction (905) to warrant proceeding with the test. If not, e.g., the patient has complete heart block, the test is terminated (910). The issue may be transient and the test may be reattempted at a later time. If intact conduction is present, at least to some degree, the test proceeds. The IMD 10 is programmed to pace at the LRI (915) and the AV delay (AP-VS or AS-VS) at this rate is recorded (920) into memory. If a patient has intact conduction, then operation at the LRI has the highest probability of success and is thus a logical starting point for the test; this is not, however, a requirement of the test. A number of cardiac cycles may pass at the test rate and the recorded AV delay may be an average of those values.

Once sufficient data at the LRI has been recorded, the atrial rate is increased (925). The test determines whether there was AV conduction (930). If not, the test may be terminated (910). Though not separately shown, rather than terminating the test, multiple attempts may be made at this rate or at other atrial rates. However, at some point a lack of AV conduction will result in the termination of the testing (910). Assuming there was AV conduction at the higher atrial rate, the AV delay is recorded and stored in memory (940). Again, multiple cardiac cycles may be monitored and averaged, or data may be obtained from a single cycle. Assuming progressively increasing atrial test rates, the next determination is whether a maximum atrial test rate has been achieved and tested (945). The maximum test rate may correlate with the IMD 10 upper rate limit (URL); however, as the testing is for purposes other than providing sustained pacing at a given rate, this maximum may exceed the URL. If the maximum atrial rate is achieved (945), the test is terminated (910). Alternatively, testing may occur until conduction fails rather than terminating at a predetermined atrial rate. Assuming the maximum atrial rate has not yet been reached (945), testing continues.

As illustrated by the "OR" box, (950), testing may take one of two pathways (and multiple test may be performed so that both approaches are taken). In a first approach, the atrial rate is again increased (925) with the remainder of the test continuing as described. In this manner, with each successive iteration, the atrial rate is rising. The amount of each increase will determine the "resolution" of the results. That is, the smaller the increment the more data collected. Conversely, the less data collected, the more extrapolation required. Increments may be made in timer interval adjustment (e.g., 10, 20, 30, 40, 50 ms increments) or by adjusting beats per minute (bpm). At 60 bpm, the A-A interval is 1000 ms, at 70 bpm the A-A interval is about 857 ms, and at 120 bpm the A-A interval is 500 ms. Thus, whatever gradation is desired in terms of direct variation of the A-A interval or in terms of bpm is utilized.

As an alternative (950), the A-A interval may be returned to the LRI for a period of time before each successive test cycle at a higher rate. This alternative may be utilized as the exclusive test mechanism or a complete test may be performed by iteratively increasing atrial rate and then separately performing a second test with a return to the LRI with each iteration. As an example, the test may for measure AV delay at the LRI (e.g., 60, bpm), then 61 bpm, then return to 60 bpm, then 62, bpm, then 60 bpm . . . 80 bpm, then 60 bpm, etc. until the maximum atrial rate is tested. Again, the time spent at the LRI and/or the test rate may be independently selected and may be one cycle or any number of cycles. The purpose of returning to the LRI is to simulate the effect of an accelerated atrial pace which would be a one cycle change from e.g., the LRI to the calculated atrial rate for one cycle. It is under these conditions that conduction and the AV delay data will most likely actually be utilized.

As indicated, the testing is performed by a clinician, most likely in a medical office setting. The results will provide data that is patient specific across the range of permissive atrial rates. In addition, those patients using a rate responsive function may also generate data on an on-going basis. Thus, at step (960) certain patients will have their IMDs operating with a rate response function. As the atrial rate varies, the corresponding AV delay and success or failure of conduction are monitored (965) and updated in memory (970). When available, this data may be more useful than the initial test results if the patient's condition has changed. Finally, it should be appreciated that the results of accelerated atrial pacing can provide data and this data may optionally be weighted due to the relevance of the results in context.

FIG. 12 is a partially completed, sample table of data that may be collected during AV conduction testing or through rate response monitoring. The first column is atrial rate in milliseconds. The second column indicates whether conduction was successful at this rate. The third column indicates what the AV delay of successful conduction was at this rate (averaged if more than one data point). It should be appreciated that at the LRI or at common rates with rate responsiveness many data points will be collected at a given rate over time. As the patient's condition may vary, these frequently updated data points may be limited to a recent subset to reflect current data (e.g., data collected in the last day, last week, etc.) rather than over the lifetime of the implant. The fourth column indicates whether the data point(s) were obtained during AV conduction testing or through rate response (may indicate the temporal relevance of the data). The fifth column indicates whether the atrial rate was reached progressively or through a single change. While not necessarily limiting, an indication that successful conduction was achieved with a large change, the likelihood of success with the accelerated atrial pace may be increased. The next column indicates whether there were multiple confirmations at this rate. This may simply indicate that during testing, the atrial rate was maintained for some number of cycles (as opposed to one); this may indicate success during rate response as well as during AV conduction testing; and/or this may indicate success during more than one AV conduction test. The end result is that success was achieved on more than one attempt. The next column indicates the percentage of successful conducted events out of the number attempted. Finally, the last column indicates whether there was success at this atrial rate recently. Recent is subjective, but will be established for a given device or by a caregiver as clinically relevant. Whether conduction needed to occur in the last day, week, month, etc. to be considered recent is a selectable parameter. This table is not meant to be limiting; the sample data shown is not required and alternative data may be included or substituted.

By using this data, a determination can be made as to whether to attempt an accelerated atrial pace at a given A-A interval. For example, testing on this patient indicates that conduction was never successful at 400 ms. Thus, logically there is no reason to attempt accelerated atrial pacing at this rate. The LRI (1000 ms), 975 ms, and 700 ms all have been shown to be successful and would be acceptable. At 650 ms, there is a high degree of success; however, no recent success. This is not necessarily troubling. First, rate response may not be enabled thereby precluding pacing at this rate (hence precluding recent success). Second, rate response may be enabled (and is since column 4 so indicated), but this rate simply has not be reached with no negative implication. Though not shown, other relevant data points could be recent failure at this rate and/or if this rate has been recently attempted. The 600 ms rate has almost the same data except that success was only achieved during initial AV conduction testing. Again, this alone is non-problematic; however, if recent failure occurred (again not illustrated) at this rate that would counsel against using this value.

Finally, at 500 ms conduction was successfully achieved but only 65% of the time attempted and there were no recent successful attempts. Again, there may not have been recent success because the rate response function never attempted to pace at this rate. Whether or not a value of 65% would permit accelerated pacing at this rate would depend on the hierarchy of values programmed by the clinician. In the simplest form, a numerical value may selected (e.g., 80%) and conduction must have been successful at this rate or higher in order to be utilized. More complex evaluations may be made. For example, a lower percentage may be acceptable if recently successful or some other factor mitigates the "low" rate of success. Of course, what value is actually selected may be clinician specific. In some cases, relatively high rates of success may be warranted (90+%); alternatively, for some a 50% rate may warrant an attempt. Finally, in some cases any degree of success may warrant an attempt at that rate. Ultimately, the data is collected and provided and the various cutoff parameters are selected by the clinician.

The present invention has been shown and described with respect to various illustrated examples, embodiments and figures. These are not meant to be limiting and one of ordinary skill in the art would appreciate that numerous variations are within the scope of the present invention.

The invention claimed is:

1. An implantable medical device (IMD) comprising:
   means for sensing cardiac data;
   means for identifying premature ventricular contractions (PVC) from the cardiac data;
   means for pacing responsive to the means for sensing;
   a ventricular pacing protocol (VPP) module for controlling the means for pacing and to prevent ventricular pacing in a given cardiac cycle wherein a ventricular sensed event occurred in a cardiac cycle immediately prior to the given cardiac cycle; and
   means for controlling a V-V interval immediately following and initiated by an identified PVC by selectively varying an A-A interval.

2. The IMD of claim 1, wherein the means for controlling the V-V interval preclude ventricular pacing to control the V-V interval.

3. The IMD of claim 1, wherein the means for controlling the V-V interval include means for determining a desired ventricular sense time and calculating an A-A interval to facilitate the desired ventricular sense time.

4. The IMD of claim 3, wherein the desired ventricular sense time results in a PVC to ventricular sense interval (V-V(2)) that is correlated with a ventricular sensed event to PVC interval (V-V(1)).

5. The IMD of claim 4, wherein the correlation is that V-V(2)=V-V(1)+a predetermined constant.

6. The IMD of claim 4, wherein the correlation is that V-V(2)=V-V(1)+(X %*V-V(1)).

7. The IMD of claim 4, further comprising means for determining an AV interval for the V-V(2) interval and the A-A interval is set to an A-AP interval wherein the AP initiates an the AV interval.

8. The IMD of claim 4, further comprising means for generating progressively longer V-V intervals immediately subsequent to V-V(2) until a pre-PVC V-V interval is achieved, wherein the pre-PVC interval is a V-V interval duration occurring in the cardiac cycle prior to that having the PVC.

9. An implantable medical device (IMD) comprising:
   a cardiac pacing module;
   a ventricular pacing protocol (VPP) module configured to control the pacing module and prevent ventricular pacing in a given cardiac cycle wherein a ventricular sensed event occurred in a cardiac cycle immediately prior to the given cardiac cycle and permit ventricular pacing in the given cardiac cycle if no ventricular event was sensed in the immediately prior cardiac cycle; and
   a ventricular interval smoothing module configured to respond to a sensed PVC and alter atrial intervals to create one or more consecutive V-V intervals having a progressively larger duration without providing ventricular pacing.

10. The IMD of claim 9, further comprising a calculation module to calculate a desired ventricular sense time, determine an appropriate A-A interval that results in the desired ventricular sense time and provides the ventricular interval smoothing modules with the A-A interval to alter the atrial interval.

11. A method comprising:
    operating a cardiac pacing device according to a ventricular pacing protocol (VPP);
    sensing a premature ventricular contraction (PVC) in a first cardiac cycle;
    measuring a duration of a first ventricular interval from a ventricular event immediately preceding the PVC to the PVC;
    calculating a duration of a second ventricular interval to occur from the PVC to a target ventricular sensed event; and
    modifying atrial timing in the first cardiac cycle to effect the second ventricular interval.

12. The method of claim 11, wherein the second ventricular interval occurs without ventricular pacing.

13. The method of claim 11, modifying atrial timing in subsequent consecutive cycles until a resultant V-V interval is substantially equal to a V-V interval prior to the first ventricular interval.

14. The method of claim 13, wherein the modification of atrial timing in subsequent consecutive cycles results in a smoothing of the resultant V-V intervals.

15. The method of claim 11, wherein calculating the duration of the second ventricular interval includes adding a constant to the duration of the first ventricular interval.

16. The method of claim 15, wherein the constant is selected from a table and the table includes constant values for corresponding ventricular intervals.

17. The method of claim 11, wherein calculating the duration of the second ventricular interval includes increasing the first ventricular interval by a predetermined percentage.

18. The method of claim 11, further comprising:
    sensing for atrial refractory events; and
    adding a predetermined value to the modified atrial timing if an atrial refractory event is sensed.

19. The method of claim 11, further comprising:
    setting a first AV interval for delivering a ventricular backup pacing pulse following an A-A interval devoid of a sensed ventricular event according to the VPP;
    setting a second AV interval for delivering a ventricular pacing pulse following a truncated A-A interval as modified to effect the second ventricular interval wherein the second AV interval is longer than the first AV interval.

20. The method of claim 11, wherein modifying the atrial timing includes determining an AV interval that would result in the target sensed ventricular event and delivering an atrial pacing pulse at so that the atrial pacing pulse initiated the AV interval.

* * * * *